(12) United States Patent
Wang

(10) Patent No.: US 8,946,445 B2
(45) Date of Patent: Feb. 3, 2015

(54) HETEROCYCLIC MOLECULES AS APOPTOSIS INDUCERS

(71) Applicant: Nanjing Allgen Pharma Co. Ltd., Nanjing (CN)

(72) Inventor: Zhaoyin Wang, Kirkland (CA)

(73) Assignee: Nanjing Allgen Pharma Co., Ltd., Nanjing (CN)

(*) Notice: Subject to any disclaimer, the term of this patent is extended or adjusted under 35 U.S.C. 154(b) by 0 days.

(21) Appl. No.: 14/351,479

(22) PCT Filed: Oct. 11, 2012

(86) PCT No.: PCT/CA2012/000942
§ 371 (c)(1),
(2) Date: Apr. 11, 2014

(87) PCT Pub. No.: WO2013/053045
PCT Pub. Date: Apr. 18, 2013

(65) Prior Publication Data
US 2014/0256768 A1    Sep. 11, 2014

Related U.S. Application Data

(60) Provisional application No. 61/627,402, filed on Oct. 12, 2011.

(51) Int. Cl.
| | |
|---|---|
| *C07D 487/02* | (2006.01) |
| *C07D 491/02* | (2006.01) |
| *C07D 495/02* | (2006.01) |
| *C07D 497/02* | (2006.01) |
| *A61N 5/10* | (2006.01) |
| *A61K 31/407* | (2006.01) |
| *A61K 31/437* | (2006.01) |
| *C07D 471/04* | (2006.01) |
| *C07D 487/04* | (2006.01) |
| *C07D 495/04* | (2006.01) |
| *A61K 45/06* | (2006.01) |
| *A61K 31/675* | (2006.01) |

(52) U.S. Cl.
CPC .............. *A61N 5/10* (2013.01); *A61K 31/407* (2013.01); *A61K 31/437* (2013.01); *C07D 471/04* (2013.01); *C07D 487/04* (2013.01); *C07D 495/04* (2013.01); *A61K 45/06* (2013.01); *A61K 31/675* (2013.01)
USPC .......................................... 548/453; 546/120

(58) Field of Classification Search
USPC .......................................... 548/453; 546/120
See application file for complete search history.

(56) References Cited

U.S. PATENT DOCUMENTS

| | | |
|---|---|---|
| 6,720,338 B2 | 4/2004 | Augeri et al. |
| 7,030,115 B2 | 4/2006 | Elmore et al. |
| 7,709,467 B2 | 5/2010 | Bruncko et al. |
| 2008/0188460 A1 | 8/2008 | Casara et al. |

FOREIGN PATENT DOCUMENTS

| | | | |
|---|---|---|---|
| CA | 2527583 C | | 12/2013 |
| WO | 2004/106328 | * | 12/2004 |
| WO | 2005/049594 A1 | | 6/2005 |
| WO | 2005/117908 A2 | | 12/2005 |
| WO | 2006/069441 A1 | | 7/2006 |

OTHER PUBLICATIONS

International Search Report corresponding to PCT/CA2012/000942 mailed Jan. 21, 2013 (5 pages).
Su, Jung-Chen et al., "Synthesis and biological activity of obatoclax derivatives as novel and potent SHP-1 agonists," *European Journal of Medicinal Chemistry* (2012) 56:127-133.
Volger, M. et al., "Bcl-2 inhibitors: small molecules with a big impact on cancer therapy,." *Cell Death and Differentiation* (2009) 16:360-367.

* cited by examiner

*Primary Examiner* — Niloofar Rahmani
(74) *Attorney, Agent, or Firm* — Kilpatrick Townsend & Stockton LLP

(57) ABSTRACT

The present document describes novel compounds which may inhibit the activity of anti-apoptotic proteins such as Bcl-2 family protein members, compositions containing the compounds and methods of treating diseases involving a defect in apoptosis, such as, for example, in the treatment of cancer.

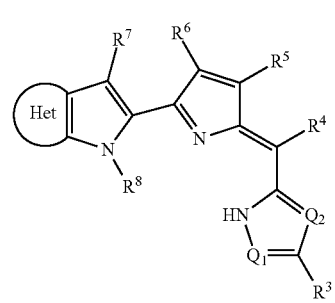

11 Claims, No Drawings

HETEROCYCLIC MOLECULES AS APOPTOSIS INDUCERS

CROSS-REFERENCE TO RELATED APPLICATIONS

This application claims priority under 35 USC§119(e) of U.S. provisional patent application 61/627,402, filed on Oct. 12, 2011 the specification of which is hereby incorporated by reference.

BACKGROUND (a) Field

The subject matter disclosed generally relates to compounds which may inhibit the activity of anti-apoptotic proteins. More specifically, the subject matter disclosed relates to compounds which may inhibit the activity of anti-apoptotic proteins such as Bcl-2 family protein members, compositions containing the compounds and methods of treating diseases involving a defect in apoptosis, such as, for example, in the treatment of cancer, or preventing a viral infection, or inhibiting the replication or infectivity of a virus (b) Related Prior Art Anti-apoptotic family protein members are associated with a number of diseases and thus are under investigation as potential therapeutic drug targets. Important targets for interventional therapy are the Bcl-2 family of proteins which include, for example, Bcl-2, Bcl-XI, Bcl-B, Bfl-1, Bcl-w and Mcl-1. A recent review described the therapeutic potential of small molecule Bcl-2 inhibitors (Vogler et al, Cell Death and Differentiation (2009) 16, 360-367). Recently inhibitors of Bcl-2 family members have been reported in the literature, see, for example, WO 2005/049594, WO 2005/117908, WO 2006/069441, U.S. Pat. Nos. 6,720,338, 7,030,115, 7,709, 467 and US2008/0188460. This invention is directed to a series of novel heterocyclic compounds that can inhibit Bcl-2 family proteins and promote apoptosis.

SUMMARY

The invention is directed to a series of novel compounds which inhibit the activity of anti-apoptotic Bcl-2 family protein members and are useful for the treatment of diseases involving a defect in apoptosis, such as, for example, in the treatment of cancer. Pharmaceutical compositions and methods of use are also included.

According to an embodiment, there is provided a compound of Formula I

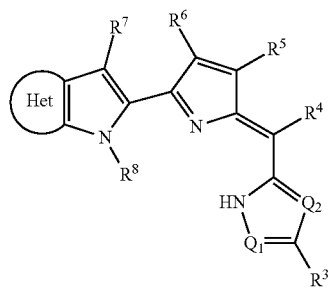

I or a pharmaceutically acceptable salt thereof, wherein:
$Q_1$ may be —C($R^1$)— or —N—;
$Q_2$ may be —C($R^2$)— or —N—;

$R^1$, $R^2$, and $R^3$ may be independently —$Y_m(R_b)$, wherein $R_b$ may be —H, halogen, —$NH_2$, —CN, —$NO_2$, —SH, —$N_3$, —$C_1$-$C_8$ alkyl, —O—($C_1$-$C_8$ alkyl), —$C_2$-$C_8$ alkenyl, —$C_2$-$C_8$ alkynyl, —$C_3$-$C_{12}$ cycloalkyl, -aryl, -heteroaryl, -3- to 9-membered heterocycle, —$OR^9$, —O($CH_2)_nOR^9$, —C(O)$R^9$, —O—C(O)$R^9$, —C(O)($CH_2)_n$—$R^9$, —O—C (O)O$R^9$, —O—C(O)NH$R^9$, —O—C(O)N($R^9)_2$, —C(O)N($R^9)_2$, —C(O)O$R^9$, —C(O)NH$R^9$, —S—$R^9$, —S(O)$R^9$, —S(O)$_2R^9$, —NHC(O)$R^9$, —NHS(O)$_2R^9$, —O—C(S)$R^9$, —O—C(S)O$R^9$, —O—C(S)NH$R^9$, —O—C(S)N($R^9)_2$, —C(S)O$R^9$, —C(S)NH$R^9$, —C(S)N($R^9)_2$, —NHC(S)$R^9$, —N$R^9$C(S)$R^9$, —NHC(S)NH$R^9$, —NHC(S)N($R^9)_2$, —N$R^9$C(S)NH$R^9$, —N$R^9$C(S)N($R^9)_2$ or $R^1$ and $R^3$, or $R^2$ and $R^3$, together with the carbon atom to which each may be attached, join to form a 5- to 9-membered ring which may be unsubstituted or substituted by 1 to 3 hetero atoms;
$R^4$ may be —H, halogen, —OH, —$NH_2$, —$C_1$-$C_8$ alkyl, or —O—($C_1$-$C_8$ alkyl);
$R^5$ may be —$Y_m$—($R_c$), wherein —$R_c$ may be —$C_1$-$C_8$ alkyl, —O—($C_1$-$C_8$ alkyl), —O-benzyl, —OH, —$NH_2$, —NH ($C_1$-$C_5$ alkyl), —N($C_1$-$C_5$ alkyl)$_2$, —NH(aryl), —N(aryl)$_2$, —NH(heteroaryl), —N(heteroaryl)$_2$, —CN, —$NO_2$, —$N_3$, —$C_2$-$C_8$ alkynyl, —$OR^9$, —O($CH_2)_nOR^9$, —C(O) $R_9$, —O—C(O)$R^9$, —C(O)($CH_2)_n$—$R^9$, —O—C(O)O$R^9$, —O—C(O)NH$R^9$, —O—C(O)N($R^9)_2$, —C(O)N($R^9)_2$, —C(O)O$R^9$, —C(O)NH$R^9$, —S—$R^9$, —S(O)$R^9$, —S(O)$_2R^9$, —NHC(O)$R^9$, —NHS(O)$_2R^9$, —O—C(S)$R^9$, —O—C(S)O$R^9$, —O—C(S)NH$R^9$, O—C(S)N($R^9)^2$, —C(S)O$R^9$, —C(S)NH$R^9$, —C(S)N($R^9$)2, —NHC(S)$R^9$, —N$R^9$C(S)$R^9$, —NHC(S)NH$R^9$, —NHC(S)N($R^9)_2$, —N$R^9$C(S)NH$R^9$, —N$R^9$C(S)N($R^9)_2$;
$R^6$ may be —$Y_m(R_d)$, wherein —$R_d$ may be —H, —OH, halogen, amino, -aryl, -heteroaryl, —NH($C_1$-$C_5$ alkyl), —N($C_1$-$C_5$ alkyl)$_2$, —NH(aryl), —N(aryl)$_2$, —NH(heteroaryl), —N(heteroaryl)$_2$, —CN, —$NO_2$, —$N_3$, —$C_1$-$C_8$ alkyl, —O—($C_1$-$C_8$ alkyl), —($C_1$-$C_8$ alkyl)-OH, —$C_2$-$C_8$ alkenyl, —$C_2$-$C_8$ alkynyl, —$C_3$-$C_{12}$ cycloalkyl, -aryl, -heteroaryl, -3- to 9-membered heterocycle, —$OR^9$, —O($CH_2)_nOR^9$, —C(O)$R^9$, —O—C(O)$R^9$, —C(O) ($CH_2)_n$—$R^9$, —O—C(O)O$R^9$, —O—C(O)NH$R^9$, —O—C(O)N($R^9$)2, —C(O)N($R^9)_2$, —C(O)O$R^9$, —C(O) NH$R^9$, —S—$R^9$, —S(O)$R^9$, —S(O)$_2R^9$, —NHC(O)$R^9$, —NHS(O)$_2R^9$, —O—C(S)$R^9$, —O—C(S)O$R^9$, —O—C (S)NH$R^9$, O—C(S)N($R^9)_2$, —C(S)O$R^9$, —C(S)NH$R^9$, —C(S)N($R^9)_2$, —NHC(S)$R^9$, —N$R^9$C(S)$R^9$, —NHC(S) NH$R^9$, —NHC(S)N($R^9)_2$, —N$R^9$C(S)NH$R^9$, —N$R^9$C(S) N($R^9)_2$;
$R^7$ may be —$Y_m(R_e)$, wherein —$R_e$ may be —H, halogen, —$NH_2$, $C_1$-$C_8$ alkyl, -aryl, -heteroaryl, —NH($C_1$-$C_5$ alkyl), —N($C_1$-$C_5$ alkyl)$_2$, —NH(aryl), —N(aryl)$_2$, —NH (heteroaryl), —N(heteroaryl)$_2$, —C(O)NH($C_1$-$C_5$ alkyl), —C(O)N($C_1$-$C_5$ alkyl)$_2$, —NHC(O)($C_1$-$C_5$ alkyl), —NHC (=$NH2^+$)$NH_2$, —CN, —$NO_2$, $N_3$, -3- to 9-membered heterocycle, —$OR^9$, —O($CH_2)_nOR^9$, —C(O)$R^9$, —O—C(O) $R^9$, —C(O)($CH_2)_n$—$R^9$, —O—C(O)O$R^9$, —O—C(O) NH$R^9$, —O—C(O)N($R^9)_2$, —C(O)N($R^9)_2$, —C(O)O$R^9$, —C(O)NH$R^9$, —S—$R^9$, —S(O)$R^9$, —S(O)$_2R^9$, —NHC (O)$R^9$, —NHS(O)$_2R^9$, —O—C(S)$R_9$, —O—C(S)O$R^9$, —O—C(S)NH$R^9$, O—C(S)N($R^9)_2$, —C(S)O$R^9$, —C(S) NH$R^9$, —C(S)N($R^9)_2$, —NHC(S)$R^9$, —N$R^9$C(S)$R^9$, —NHC(S)NH$R^9$, —NHC(S)N($R^9)_2$, —N$R^9$C(S)NH$R^9$, —N$R^9$C(S)N($R^9)_2$;
$R^8$ may be —$Y_m(R_a)$, wherein —$R_a$ may be —H, —OH, —$C_1$-$C_8$ alkyl, —$C_2$-$C_8$ alkenyl, —$C_2$-$C_8$ alkynyl, —$C_3$-$C_{12}$ cycloalkyl, -aryl, -heteroaryl, -3- to 9-membered heterocycle, —$OR^9$, —O($CH_2)_nOR^9$, —C(O)$R^9$, —O—C(O) $R^9$, —C(O)($CH_2)_n$—$R^9$, —O—C(O)O$R^9$, —O—C(O)

—NHR⁹, —O—C(O)N(R⁹)₂, —C(O)N(R⁹)₂, —C(O)OR⁹, —C(O)NHR⁹, —S—R⁹, —S(O)R⁹, —S(O)₂R⁹, —NHC(O)R⁹, —NHS(O)₂R⁹, —O—C(S)R⁹, —O—C(S)OR⁹, —O—C(S)NHR⁹, O—C(S)N(R⁹)₂, —C(S)R⁹, —C(S)OR⁹, —C(S)NHR⁹, —C(S)N(R⁹)₂, —NHC(S)R⁹, —NR⁹C(S)R⁹, —NHC(S)NHR⁹, —NHC(S)N(R⁹)₂, —NR⁹C(S)NHR⁹, —NR⁹C(S)N(R⁹)₂;

R⁹ may be independently —H, —C₁-C₈ alkyl, —C₃-C₁₂ cycloalkyl, -aryl, -heteroaryl, -3- to 9-membered heterocycle, —C₂-C₈ alkenyl, or —C₂-C₈ alkynyl;
wherein

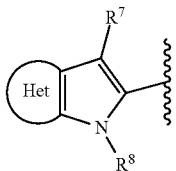

may be selected from the from the following 6,5-bicyclic moieties:

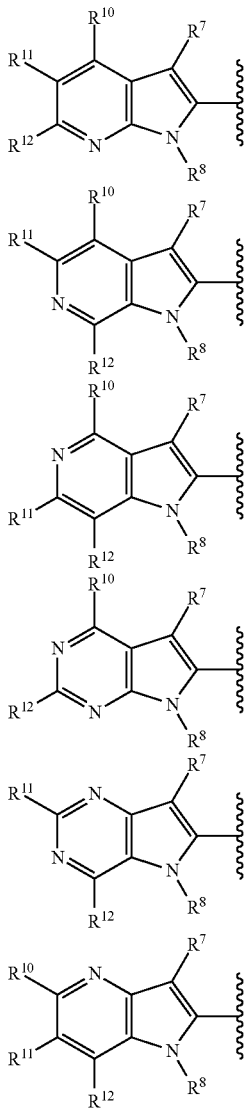

wherein
R¹⁰, R¹¹ and R¹² may be independently —Yₘ(R_f), wherein —R_f may be —H, halogen, —NH₂, C₁-C₈ alkyl, —NH(C₁-C₈ alkyl), —N(C₁-C₈ alkyl)₂, -aryl, -heteroaryl, —NH(aryl), —N(aryl)₂, —NH(heteroaryl), —N(heteroaryl)₂, —C(O)NH(C₁-C₈ alkyl), —C(O)N(C₁-C₈ alkyl)₂, —NHC(O)(C₁-C₈ alkyl), —NHC(=NH₂⁺)NH₂, —CN, —NO₂, N₃, -3- to 9-membered heterocycle, —OR⁹, —O(CH₂)ₙOR⁹, —C(OH)R⁹₂, —CH(OH)R⁹, —C(O)R⁹, —O—C(O)R⁹, —C(O)(CH₂)ₙ—R⁹, —O—C(O)OR⁹, —O—C(O)NHR⁹, —O—C(O)N(R⁹)₂, —C(O)N(R⁹)₂, —C(O)OR⁹, —C(O)NHR⁹, —S—R⁹, —S(O)R⁹, —S(O)₂R⁹, —NHC(O)R⁹, —NHS(O)₂R⁹, —O—C(S)R⁹, —O—C(S)OR⁹, —O—C(S)NHR⁹, O—C(S)N(R⁹)₂, —C(S)OR⁹, —C(S)NHR⁹, —C(S)N(R⁹)₂, —NHC(S)R⁹, —NR⁹C(S)R⁹, —NHC(S)NHR⁹, —NHC(S)N(R⁹)₂, —NR⁹C(S)NHR⁹, —NR⁹C(S)N(R⁹)₂;

wherein when R¹⁰ and R¹¹, or R¹¹ and R¹² may be next to each other, together with the carbon atom to which each may be attached, may join to form a 5- to 9-membered carbocycle or heterocycle;

each Y may be independently —C₁-C₈ alkylene-, —C₂-C₈ alkenylene- or —C₂-C₈ alkynylene-;

each m may be independently 0 or 1; and each n may be independently an integer ranging from 0 to 6.

According to another embodiment, there is provided a compound of Formula II

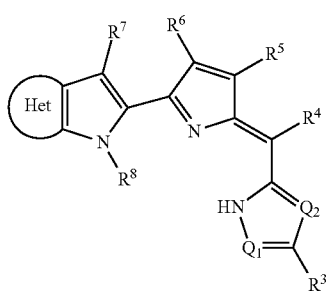

II or a pharmaceutically acceptable salt thereof, wherein:
Q₁ may be —C(R¹)— or —N—;
Q₂ may be —C(R²)— or —N—;
R¹, R², and R³ may be independently —Yₘ(R_b), wherein R_b may be —H, halogen, —NH₂, —CN, —NO₂, —SH, —N₃, —C₁-C₈ alkyl, —O—(C₁-C₈ alkyl), —C₂-C₈ alkenyl, —C₂-C₈ alkynyl, —C₃-C₁₂ cycloalkyl, -aryl, -heteroaryl, -3- to 9-membered heterocycle, —OR⁹, —O(CH₂)ₙOR⁹, —C(O)R⁹, —O—C(O)R⁹, —C(O)(CH₂)ₙ—R⁹, —O—C(O)OR⁹, —O—C(O)NHR⁹, —O—C(O)N(R⁹)₂, —C(O)N(R⁹)₂, —C(O)OR⁹, —C(O)NHR⁹, —S—R⁹, —S(O)R⁹, —S(O)₂R⁹, —NHC(O)R⁹, —NHS(O)₂R⁹, —O—C(S)R⁹, —O—C(S)OR⁹, —O—C(S)NHR⁹, O—C(S)N(R⁹)₂, —C(S)OR⁹, —C(S)NHR⁹, —C(S)N(R⁹)₂, —NHC(S)R⁹, —NR⁹C(S)R⁹, —NHC(S)NHR⁹, —NHC(S)N(R⁹)₂, —NR⁹C(S)NHR⁹, —NR⁹C(S)N(R⁹)₂ or R¹ and R³, or R² and R³, together with the carbon atom to which each may be attached, may join to form a 5- to 9-membered ring which may be unsubstituted or substituted by 1 to 3 hetero atoms;

R⁴ may be —H, halogen, —OH, —NH₂, —C₁-C₈ alkyl, or —O—(C₁-C₈ alkyl);

R⁵ may be —Yₘ—(R_c), wherein —R_c may be —C₁-C₈ alkyl, —O—(C₁-C₈ alkyl), —O-benzyl, —OH, —NH₂, —NH(C₁-C₅ alkyl), —N(C₁-C₅ alkyl)₂, —NH(aryl), —N(aryl)₂, —NH(heteroaryl), —N(heteroaryl)₂, —CN, —NO₂, —N₃, —C₂-C₈ alkynyl, —OR⁹, —O(CH₂)ₙOR⁹, —C(O)R₉, —O—C(O)R⁹, —C(O)(CH₂)ₙ—R⁹, —O—C(O)OR⁹, —O—C(O)NHR⁹, —O—C(O)N(R⁹)₂, —C(O)N(R⁹)₂, —C(O)OR⁹, —C(O)NHR⁹, —S—R⁹, —S(O)R⁹, —S(O)₂R⁹, —NHC(O)R⁹, —NHS(O)₂R⁹, —O—C(S)R⁹, —O—C(S)OR⁹, —O—C(S)NHR⁹, O—C(S)N(R⁹)², —C(S)OR⁹, —C(S)NHR⁹, —C(S)N(R⁹)2, —NHC(S)R⁹, —NR⁹C(S)R⁹, —NHC(S)NHR⁹, —NHC(S)N(R⁹)₂, —NR⁹C(S)NHR⁹, —NR⁹C(S)N(R⁹)₂;

R⁶ may be —Y_m(R_d), wherein —R_d may be —H, —OH, halogen, amino, -aryl, -heteroaryl, —NH(C₁-C₅ alkyl), —N(C₁-C₈ alkyl)₂, —NH(aryl), —N(aryl)₂, —NH(heteroaryl), —N(heteroaryl)₂, —CN, —NO₂, —N₃, —C₁-C₈ alkyl, —O—(C₁-C₈ alkyl), —(C₁-C₈ alkyl)-OH, —C₂-C₈ alkenyl, —C₂-C₈ alkynyl, —C₃-C₁₂ cycloalkyl, -aryl, heteroaryl, -3- to 9-membered heterocycle, —OR⁹, —O(CH₂)_nOR⁹, —C(O)R⁹, —O—C(O)R⁹, —C(O)(CH₂)_n—R⁹, —O—C(O)OR⁹, —O—C(O)NHR⁹, —O—C(O)N(R⁹)2, —C(O)N(R⁹)₂, —C(O)OR⁹, —C(O)NHR⁹, —S—R⁹, —S(O)R⁹, —S(O)₂R⁹, —NHC(O)R⁹, —NHS(O)₂R⁹, —O—C(S)R⁹, —O—C(S)OR⁹, —O—C(S)NHR⁹, O—C(S)N(R⁹)₂, —C(S)OR⁹, —C(S)NHR⁹, —C(S)N(R⁹)₂, —NHC(S)R⁹, —NR⁹C(S)R⁹, —NHC(S)NHR⁹, —NHC(S)N(R⁹)₂, —NR⁹C(S)NHR⁹, —NR⁹C(S)N(R⁹)₂;

R⁷ may be —Y_m(R_e), wherein —R_e may be —H, halogen, —NH₂, C₁-C₈ alkyl, -aryl, -heteroaryl, —NH(C₁-C₅ alkyl), —N(C₁-C₅ alkyl)₂, —NH(aryl), —N(aryl)₂, —NH(heteroaryl), —N(heteroaryl)₂, —C(O)NH(C₁-C₅ alkyl), —C(O)N(C₁-C₅ alkyl)₂, —NHC(O)(C₁-C₈ alkyl), —NHC(=NH2⁺)NH₂, —CN, —NO₂, N₃, -3- to 9-membered heterocycle, —OR⁹, —O(CH₂)OR⁹, —C(O)R⁹, —O—C(O)R⁹, —C(O)(CH₂)_n—R⁹, —O—C(O)OR⁹, —O—C(O)NHR⁹, —O—C(O)N(R⁹)₂, —C(O)N(R⁹)₂, —C(O)OR⁹, —C(O)NHR⁹, —S—R⁹, —S(O)R⁹, —S(O)₂R⁹, —NHC(O)R⁹, —NHS(O)₂R⁹, —O—C(S)R₉, —O—C(S)OR⁹, —O—C(S)NHR⁹, O—C(S)N(R⁹)₂, —C(S)OR⁹, —C(S)NHR⁹, —C(S)N(R⁹)₂, —NHC(S)R⁹, —NR⁹C(S)R⁹, —NHC(S)NHR⁹, —NHC(S)N(R⁹)₂, —NR⁹C(S)NHR⁹, —NR⁹C(S)N(R⁹)₂;

R⁸ may be —Y_m(R_a), wherein —R_a may be —H, —OH, —C₁-C₈ alkyl, —C₂-C₈ alkenyl, —C₂-C₈ alkynyl, —C₃-C₁₂ cycloalkyl, -aryl, -heteroaryl, -3- to 9-membered heterocycle, —OR⁹, —O(CH₂)_nOR⁹, —C(O)R⁹, —O—C(O)R⁹, —C(O)(CH₂)_n—R⁹, —O—C(O)OR⁹, —O—C(O)NHR⁹, —O—C(O)N(R⁹)², —C(O)N(R⁹)₂, —C(O)OR⁹, —C(O)NHR⁹, —S—R⁹, —S(O)R⁹, —S(O)₂R⁹, —NHC(O)R⁹, —NHS(O)₂R⁹, —O—C(S)R⁹, —O—C(S)OR⁹, —O—C(S)NHR⁹, O—C(S)N(R⁹)₂, —C(S)OR⁹, —C(S)NHR⁹, —C(S)N(R⁹)₂, —NHC(S)R⁹, —NR⁹C(S)R⁹, —NHC(S)NHR⁹, —NHC(S)N(R⁹)₂, —NR⁹C(S)NHR⁹, —NR⁹C(S)N(R⁹)₂;

R⁹ may be independently —H, —C₁-C₈ alkyl, —C₃-C₁₂ cycloalkyl, -aryl, -heteroaryl, -3- to 9-membered heterocycle, —C₂-C₈ alkenyl, or —C₂-C₈ alkynyl;

wherein

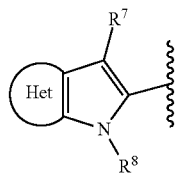

may be selected from the from the following 5,5-bicyclic moieties:

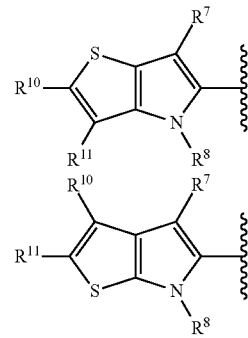

wherein

R¹⁰, and R¹¹ may be independently —Y_m(R_f), wherein —R_f may be —H, halogen, —NH₂, C₁-C₈ alkyl, —NH(C₁-C₅ alkyl), —N(C₁-C₅ alkyl)₂, -aryl, -heteroaryl, —NH(aryl), —N(aryl)₂, —NH(heteroaryl), —N(heteroaryl)₂, —C(O)NH(C₁-C₅ alkyl), —C(O)N(C₁-C₅ alkyl)₂, —NHC(O)(C₁-C₅ alkyl), —NHC(=NH₂⁺)NH₂, —CN, —NO₂, N₃, -3- to 9-membered heterocycle, —OR⁹, —O(CH₂)_nOR⁹, —C(OH)R⁹₂, —CH(OH)R⁹, —C(O)R⁹, —O—C(O)R⁹, —C(O)(CH₂)_n—R⁹, —O—C(O)OR⁹, —O—C(O)NHR⁹, —O—C(O)N(R⁹)₂, —C(O)N(R⁹)₂, —C(O)OR⁹, —C(O)NHR⁹, —S—R⁹, —S(O)R⁹, —S(O)₂R⁹, —NHC(O)R⁹, —NHS(O)₂R⁹, —O—C(S)R⁹, —O—C(S)OR⁹, —O—C(S)NHR⁹, O—C(S)N(R⁹)₂, —C(S)OR⁹, —C(S)NHR⁹, —C(S)N(R⁹)₂, —NHC(S)R⁹, —NR⁹C(S)R⁹, —NHC(S)NHR⁹, —NHC(S)N(R⁹)₂, —NR⁹C(S)NHR⁹, —NR⁹C(S)N(R⁹)₂;

wherein when R¹⁰ and R¹¹ together with the carbon atom to which each may be attached, may join to form a 5- to 9-membered carbocycle or heterocycle;

each Y may be independently —C₁-C₈ alkylene-, —C₂-C₈ alkenylene- or —C₂-C₈ alkynylene-;

each m may be independently 0 or 1; and each n may be independently an integer ranging from 0 to 6.

According to another embodiment, there is provided a compound of Formula IIa

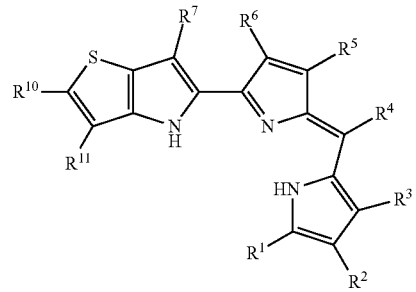

or a pharmaceutically acceptable salt thereof, wherein:

R¹, R², and R³ may be independently —Y_m(R_b), wherein R_b may be —H, halogen, —NH₂, —CN, —NO₂, —SH, —N₃, —C₁-C₈ alkyl, —O—(C₁-C₈ alkyl), —C₂-C₈ alkenyl, —C₂-C₈ alkynyl, —C₃-C₁₂ cycloalkyl, -aryl, -heteroaryl, -3- to 9-membered heterocycle, —OR⁹, —O(CH₂)_nOR⁹, —C(O)R⁹, —O—C(O)R⁹, —C(O)(CH₂)_n—R⁹, —O—C(O)OR⁹, —O—C(O)NHR⁹, —O—C(O)N(R⁹)₂, —C(O)N(R⁹)₂, —C(O)OR⁹, —C(O)NHR⁹, —S—R⁹, —S(O)R⁹, —S(O)₂R⁹, —NHC(O)R⁹, —NHS(O)₂R⁹, —O—C(S)R⁹, —O—C(S)OR$^9$, —O—C(S)NHR$^9$, O—C(S)N(R$^9$)$_2$, —C(S)OR$^9$, —C(S)NHR$^9$, —C(S)N(R$^9$)$_2$, —NHC(S)R$^9$, —NR$^9$C(S)R$^9$, —NHC(S)NHR$^9$, —NHC(S)N(R$^9$)$_2$, —NR$^9$C(S)NHR$^9$, —NR$^9$C(S)N(R$^9$)$_2$ or R$^1$ and R$^3$, or R$^2$ and R$^3$, together with the carbon atom to which each may be attached, may join to form a 5- to 9-membered ring which may be unsubstituted or substituted by 1 to 3 hetero atoms, R$^4$ may be may be —H, halogen, —OH, —NH$_2$, —C$_1$-C$_8$ alkyl, or —O—(C$_1$-C$_8$ alkyl);

R$^5$ may be —Y$_m$—(R$_c$), wherein —R$_c$ may be —C$_1$-C$_8$ alkyl, —O—(C$_1$-C$_8$ alkyl), —O-benzyl, —OH, —NH$_2$, —NH(C$_1$-C$_5$ alkyl), —N(C$_1$-C$_5$ alkyl)$_2$, —NH(aryl), —N(aryl)$_2$, —NH(heteroaryl), —N(heteroaryl)$_2$, —CN, —NO$_2$, —N$_3$, —C$_2$-C$_8$ alkynyl, —OR$^9$, —O(CH$_2$)$_n$OR$^9$, —C(O)R$_9$, —O—C(O)R$^9$, —C(O)(CH$_2$)$_n$—R$^9$, —O—C(O)OR$^9$, —O—C(O)NHR$^9$, —O—C(O)N(R$^9$)$_2$, —C(O)N(R$^9$)$_2$, —C(O)OR$^9$, —C(O)NHR$^9$, —S—R$^9$, —S(O)R$^9$, —S(O)$_2$R$^9$, —NHC(O)R$^9$, —NHS(O)$_2$R$^9$, —O—C(S)R$^9$, —O—C(S)OR$^9$, —O—C(S)NHR$^9$, O—C(S)N(R$^9$)$^2$, —C(S)OR$^9$, —C(S)NHR$^9$, —C(S)N(R$^9$)2, —NHC(S)R$^9$, —NR$^9$C(S)R$^9$, —NHC(S)NHR$^9$, —NHC(S)N(R$^9$)$_2$, —NR$^9$C(S)NHR$^9$, —NR$^9$C(S)N(R$^9$)$_2$;

R$^6$ may be —Y$_m$(R$_d$), wherein —R$_d$ may be —H, —OH, halogen, amino, -aryl, -heteroaryl, —NH(C$_1$-C$_8$ alkyl), —N(C$_1$-C$_8$ alkyl)$_2$, —NH(aryl), —N(aryl)$_2$, —NH(heteroaryl), —N(heteroaryl)$_2$, —CN, —NO$_2$, —N$_3$, —C$_1$-C$_8$ alkyl, —O—(C$_1$-C$_8$ alkyl), —(C$_1$-C$_8$ alkyl)-OH, —C$_2$-C$_8$ alkenyl, —C$_2$-C$_8$ alkynyl, —C$_3$-C$_{12}$ cycloalkyl, -aryl, -heteroaryl, -3- to 9-membered heterocycle, —OR$^9$, —O(CH$_2$)$_n$OR$^9$, —C(O)R$^9$, —O—C(O)R$^9$, —C(O)(CH$_2$)$_n$—R$^9$, —O—C(O)OR$^9$, —O—C(O)NHR$^9$, —O—C(O)N(R$^9$)2, —C(O)N(R$^9$)$_2$, —C(O)OR$^9$, —C(O)NHR$^9$, —S—R$^9$, —S(O)R$^9$, —S(O)$_2$R$^9$, —NHC(O)R$^9$, NHS(O)$_2$R$^9$, —O—C(S)R$^9$, —O—C(S)OR$^9$, —O—C(S)NHR$^9$, O—C(S)N(R$^9$)$_2$, —C(S)OR$^9$, —C(S)NHR$^9$, —C(S)N(R$^9$)$_2$, —NHC(S)R$^9$, —NR$^9$C(S)R$^9$, —NHC(S)NHR$^9$, —NHC(S)N(R$^9$)$_2$, —NR$^9$C(S)NHR$^9$, —NR$^9$C(S)N(R$^9$)$_2$;

R$^7$ may be —Y$_m$(R$_e$), wherein —R$_e$ may be —H, halogen, —NH$_2$, C$_1$-C$_8$ alkyl, -aryl, -heteroaryl, —NH(C$_1$-C$_8$ alkyl), —N(C$_1$-C$_8$ alkyl)$_2$, —NH(aryl), —N(aryl)$_2$, —NH(heteroaryl), —N(heteroaryl)$_2$, —C(O)NH(C$_1$-C$_8$ alkyl), —C(O)N(C$_1$-C$_8$ alkyl)$_2$, —NHC(O)(C$_1$-C$_8$ alkyl), —NHC(=NH2$^+$)NH$_2$, —CN, —NO$_2$, N$_3$, -3- to 9-membered heterocycle, —OR$^9$, —O(CH$_2$)$_n$OR$^9$, —C(O)R$^9$, —O—C(O)R$^9$, —C(O)(CH$_2$)$_n$—R$^9$, —O—C(O)OR$^9$, —O—C(O)NHR$^9$, —O—C(O)N(R$^9$)$_2$, —C(O)N(R$^9$)$_2$, —C(O)OR$^9$, —C(O)NHR$^9$, —S—R$^9$, —S(O)R$^9$, —S(O)$_2$R$^9$, —NHC(O)R$^9$, —NHS(O)$_2$R$^9$, —O—C(S)R$_9$, —O—C(S)OR$^9$, —O—C(S)NHR$^9$, O—C(S)N(R$^9$)$_2$, —C(S)OR$^9$, —C(S)NHR$^9$, —C(S)N(R$^9$)$_2$, —NHC(S)R$^9$, —NR$^9$C(S)R$^9$, —NHC(S)NHR$^9$, NHC(S)N(R$^9$)$_2$, —NR$^9$C(S)NHR$^9$, —NR$^9$C(S)N(R$^9$)$_2$;

R$^9$ may be independently —H, —C$_1$-C$_8$ alkyl, —C$_1$-C$_8$ halogenated-alkyl, —C$_3$-C$_{12}$ cycloalkyl, -aryl, -heteroaryl, -3- to 9-membered heterocycle, —C$_2$-C$_8$ alkenyl, or —C$_2$-C$_8$ alkynyl;

R$^{10}$, and R$^{11}$ may be independently —Y$_m$(R$_f$), wherein —R$_f$ may be —H, halogen, —NH$_2$, C$_1$-C$_8$ alkyl, —NH(C$_1$-C$_8$ alkyl), —N(C$_1$-C$_8$ alkyl)$_2$, -aryl, -heteroaryl, —NH(aryl), —N(aryl)$_2$, —NH(heteroaryl), —N(heteroaryl)$_2$, —C(O)NH(C$_1$-C$_8$ alkyl), —C(O)N(C$_1$-C$_8$ alkyl)$_2$, —NHC(O)(C$_1$-C$_8$ alkyl), —NHC(=NH$_2$$^+$)NH$_2$, —CN, —NO$_2$, N$_3$, -3- to 9-membered heterocycle, —OR$^9$, —O(CH$_2$)$_n$OR$^9$, —C(OH)R$^9$$_2$, —CH(OH)R$^9$, —C(O)R$^9$, —O—C(O)R$^9$, —C(O)(CH$_2$)$_n$—R$^9$, —O—C(O)OR$^9$, —O—C(O)NHR$^9$, —O—C(O)N(R$^9$)$_2$, —C(O)N(R$^9$)$_2$, —C(O)OR$^9$, —C(O) NHR$^9$, —S—R$^9$, —S(O)R$^9$, —S(O)$_2$R$^9$, —NHC(O)R$^9$, —NHS(O)$_2$R$^9$, —O—C(S)R$^9$, —O—C(S)OR$^9$, —O—C(S)NHR$^9$, O—C(S)N(R$^9$)$_2$, —C(S)OR$^9$, —C(S)NHR$^9$, —C(S)N(R$^9$)$_2$, —NHC(S)R$^9$, —NR$^9$C(S)R$^9$, —NHC(S) NHR$^9$, —NHC(S)N(R$^9$)$_2$, —NR$^9$C(S)NHR$^9$, —NR$^9$C(S)N(R$^9$)$_2$;

R$^{10}$ and R$^{11}$, together with the carbon atom to which each may be attached, can form a 5- to 9-membered carbocycle or heterocycle;

each Y may be independently —C$_1$-C$_8$ alkylene-, —C$_2$-C$_8$ alkenylene- or —C$_2$-C$_8$ alkynylene-;

each m may be independently 0 or 1; and each n may be independently an integer ranging from 0 to 6.

According to another embodiment, there is provided a compound of Formula IIb

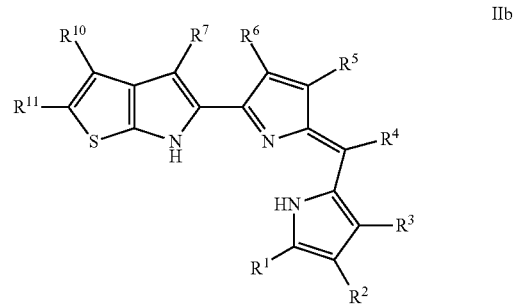

IIb or a pharmaceutically acceptable salt thereof, wherein:

R$^1$, R$^2$, and R$^3$ may be independently —Y$_m$(R$_b$), wherein R$_b$ may be —H, halogen, —NH$_2$, —CN, —NO$_2$, —SH, —N$_3$, —C$_1$-C$_8$ alkyl, —O—(C$_1$-C$_8$ alkyl), —C$_2$-C$_8$ alkenyl, —C$_2$-C$_8$ alkynyl, —C$_3$-C$_{12}$ cycloalkyl, -aryl, -heteroaryl, -3- to 9-membered heterocycle, —OR$^9$, —O(CH$_2$)$_n$OR$^9$, —C(O)R$^9$, —O—C(O)R$^9$, —C(O)(CH$_2$)$_n$—R$^9$, —O—C(O)OR$^9$, —O—C(O)NHR$^9$, —O—C(O)N(R$^9$)$_2$, —C(O)N(R$^9$)$_2$, —C(O)OR$^9$, —C(O)NHR$^9$, —S—R$^9$, —S(O)R$^9$, —S(O)$_2$R$^9$, —NHC(O)R$^9$, —NHS(O)$_2$R$^9$, —O—C(S)R$^9$, —O—C(S)OR$^9$, —O—C(S)NHR$^9$, O—C(S)N(R$^9$)$_2$, —C(S)OR$^9$, —C(S)NHR$^9$, —C(S)N(R$^9$)$_2$, —NHC(S)R$^9$, —NR$^9$C(S)R$^9$, —NHC(S)NHR$^9$, —NHC(S)N(R$^9$)$_2$, —NR$^9$C(S)NHR$^9$, —NR$^9$C(S)N(R$^9$)$_2$ or R$^1$ and R$^3$, or R$^2$ and R$^3$, together with the carbon atom to which each may be attached, join to form a 5- to 9-membered ring which may be unsubstituted or substituted by 1 to 3 hetero atoms, R$^4$ may be may be —H, halogen, —OH, —NH$_2$, —C$_1$-C$_8$ alkyl, or —O—(C$_1$-C$_8$ alkyl);

R$^5$ may be —Y$_m$—(R$_c$), wherein —R$_c$ may be —C$_1$-C$_8$ alkyl, —O—(C$_1$-C$_8$ alkyl), —O-benzyl, —OH, —NH$_2$, —NH(C$_1$-C$_5$ alkyl), —N(C$_1$-C$_5$ alkyl)$_2$, —NH(aryl), —N(aryl)$_2$, —NH(heteroaryl), —N(heteroaryl)$_2$, —CN, —NO$_2$, —N$_3$, —C$_2$-C$_8$ alkynyl, —OR$^9$, —O(CH$_2$)$_n$OR$^9$, —C(O)R$_9$, —O—C(O)R$^9$, —C(O)(CH$_2$)$_n$—R$^9$, —O—C(O)OR$^9$, —O—C(O)NHR$^9$, —O—C(O)N(R$^9$)$_2$, —C(O)N(R$^9$)$_2$, —C(O)OR$^9$, —C(O)NHR$^9$, —S—R$^9$, —S(O)R$^9$, —S(O)$_2$R$^9$, —NHC(O)R$^9$, —NHS(O)$_2$R$^9$, —O—C(S)R$^9$, —O—C(S)OR$^9$, —O—C(S)NHR$^9$, O—C(S)N(R$^9$)$^2$, —C(S)OR$^9$, —C(S)NHR$^9$, —C(S)N(R$^9$)2, —NHC(S)R$^9$, —NR$^9$C(S)R$^9$, —NHC(S)NHR$^9$, —NHC(S)N(R$^9$)$_2$, —NR$^9$C(S)NHR$^9$, —NR$^9$C(S)N(R$^9$)$_2$;

R$^6$ may be —Y$_m$(R$_d$), wherein —R$_d$ may be —H, —OH, halogen, amino, -aryl, -heteroaryl, —NH(C$_1$-C$_5$ alkyl), —N(C$_1$-C$_5$ alkyl)$_2$, —NH(aryl), —N(aryl)$_2$, —NH(heteroaryl), —N(heteroaryl)$_2$, —CN, —NO$_2$, —N$_3$, —C$_1$-C$_8$ alkyl, —O—($C_1$-$C_8$ alkyl), —($C_1$-$C_8$ alkyl)-OH, —$C_2$-$C_8$ alkenyl, —$C_2$-$C_8$ alkynyl, —$C_3$-$C_{12}$ cycloalkyl, -aryl, -heteroaryl, -3- to 9-membered heterocycle, —$OR^9$, —O($CH_2$)$_n$$OR^9$, —C(O)$R^9$, —O—C(O)$R^9$, —C(O)($CH_2$)$_n$—$R^9$, —O—C(O)$OR^9$, —O—C(O)$NHR^9$, —O—C(O)N($R^9$)2, —C(O)N($R^9$)$_2$, —C(O)$OR^9$, —C(O)$NHR^9$, —S—$R^9$, —S(O)$R^9$, —S(O)$_2$$R^9$, —NHC(O)$R^9$, —NHS(O)$_2$$R^9$, —O—C(S)$R^9$, —O—C(S)$OR^9$, —O—C(S)$NHR^9$, O—C(S)N($R^9$)$_2$, —C(S)$OR^9$, —C(S)$NHR^9$, —C(S)N($R^9$)$_2$, —NHC(S)$R^9$, —$NR^9$C(S)$R^9$, —NHC(S)$NHR^9$, —NHC(S)N($R^9$)$_2$, —$NR^9$C(S)$NHR^9$, —$NR^9$C(S)N($R^9$)$_2$;

$R^7$ may be —$Y_m$($R_e$), wherein —$R_e$ may be —H, halogen, —$NH_2$, $C_1$-$C_8$ alkyl, -aryl, -heteroaryl, —NH($C_1$-$C_5$ alkyl), —N($C_1$-$C_5$ alkyl)$_2$, —NH(aryl), —N(aryl)$_2$, —NH(heteroaryl), —N(heteroaryl)$_2$, —C(O)NH($C_1$-$C_5$ alkyl), —C(O)N($C_1$-$C_5$ alkyl)$_2$, —NHC(O)($C_1$-$C_5$ alkyl), —NHC(=$NH2^+$)$NH_2$, —CN, —$NO_2$, $N_3$, -3- to 9-membered heterocycle, —$OR^9$, —O($CH_2$)$_n$$OR^9$, —C(O)$R^9$, —O—C(O)$R^9$, —C(O)($CH_2$)$_n$—$R^9$, —O—C(O)$OR^9$, —O—C(O)$NHR^9$, —O—C(O)N($R^9$)$_2$, —C(O)N($R^9$)$_2$, —C(O)$OR^9$, —C(O)$NHR^9$, —S—$R^9$, —S(O)$R^9$, —S(O)$_2$$R^9$, —NHC(O)$R^9$, —NHS(O)$_2$$R^9$, —O—C(S)$R_9$, —O—C(S)$OR^9$, —O—C(S)$NHR^9$, O—C(S)N($R^9$)$_2$, —C(S)$OR^9$, —C(S)$NHR^9$, —C(S)N($R^9$)$_2$, —NHC(S)$R^9$, —$NR^9$C(S)$R^9$, —NHC(S)$NHR^9$, —NHC(S)N($R^9$)$_2$, —$NR^9$C(S)$NHR^9$, —$NR^9$C(S)N($R^9$)$_2$;

$R^9$ may be independently —H, —$C_1$-$C_8$ alkyl, —$C_3$-$C_{12}$ cycloalkyl, —$C_1$-$C_8$ halogenated-alkyl, -aryl, -heteroaryl, -3- to 9-membered heterocycle, —$C_2$-$C_8$ alkenyl, or —$C_2$-$C_8$ alkynyl;

$R^{10}$, and $R^1$ may be independently —$Y_m$($R_f$), wherein —$R_f$ may be —H, halogen, —$NH_2$, $C_1$-$C_8$ alkyl, —NH($C_1$-$C_5$ alkyl), —N($C_1$-$C_5$ alkyl)$_2$, -aryl, -heteroaryl, —NH(aryl), —N(aryl)$_2$, —NH(heteroaryl), —N(heteroaryl)$_2$, —C(O)NH($C_1$-$C_5$ alkyl), —C(O)N($C_1$-$C_5$ alkyl)$_2$, —NHC(O)($C_1$-$C_5$ alkyl), —NHC(=$NH_2^+$)$NH_2$, —CN, —$NO_2$, $N_3$, -3- to 9-membered heterocycle, —$OR^9$, —O($CH_2$)$_n$$OR^9$, —C(OH)$R^9$$_2$, —CH(OH)$R^9$, —C(O)$R^9$, —O—C(O)$R^9$, —C(O)($CH_2$)$_n$—$R^9$, —O—C(O)$OR^9$, —O—C(O)$NHR^9$, —O—C(O)N($R^9$)$_2$, —C(O)N($R^9$)$_2$, —C(O)$OR^9$, —C(O)$NHR^9$, —S—$R^9$, —S(O)$R^9$, —S(O)$_2$$R^9$, —NHC(O)$R^9$, —NHS(O)$_2$$R^9$, —O—C(S)$R^9$, —O—C(S)$OR^9$, —O—C(S)$NHR^9$, O—C(S)N($R^9$)$_2$, —C(S)$OR^9$, —C(S)$NHR^9$, —C(S)N($R^9$)$_2$, —NHC(S)$R^9$, —$NR^9$C(S)$R^9$, —NHC(S)$NHR^9$, —NHC(S)N($R^9$)$_2$, —$NR^9$C(S)$NHR^9$, —$NR^9$C(S)N($R^9$)$_2$;

$R^{10}$ and $R^{11}$, together with the carbon atom to which each may be attached, can form a 5- to 9-membered carbocycle or heterocycle;

each Y may be independently —$C_1$-$C_8$ alkylene-, —$C_2$-$C_8$ alkenylene- or —$C_2$-$C_8$ alkynylene-;

each m may be independently 0 or 1; and each n may be independently an integer ranging from 0 to 6.

The compound of the present invention may be selected from:

(Z)-2-(2-((3,5-dimethyl-1H-pyrrol-2-yl)methylene)-3-methoxy-2H-pyrrol-5-yl)-1H-pyrrolo[2,3-c]pyridine;

(Z)-2-(2-((3,5-dimethyl-1H-pyrrol-2-yl)methylene)-3-methoxy-2H-pyrrol-5-yl)-1H-pyrrolo[3,2-c]pyridine;

(Z)-2-(2-((3,5-dimethyl-1H-pyrrol-2-yl)methylene)-3-methoxy-2H-pyrrol-5-yl)-1H-pyrrolo[3,2-b]pyridine;

(Z)-5-(2-((3,5-dimethyl-1H-pyrrol-2-yl)methylene)-3-methoxy-2H-pyrrol-5-yl)-4H-thieno[3,2-b]pyrrole (Z)-2-chloro-5-(2-((3,5-dimethyl-1H-pyrrol-2-yl)methylene)-3-methoxy-2H-pyrrol-5-yl)-4H-thieno[3,2-b]pyrrole;

(Z)-5-(2-((3,5-dimethyl-1H-pyrrol-2-yl)methylene)-3-methoxy-2H-pyrrol-5-yl)-2-methyl-4H-thieno[3,2-b]pyrrole;

(Z)-2-bromo-5-(2-((3,5-dimethyl-1H-pyrrol-2-yl)methylene)-3-methoxy-2H-pyrrol-5-yl)-4H-thieno[3,2-b]pyrrole;

(Z)-5-(2-((3,5-dimethyl-1H-pyrrol-2-yl)methylene)-3-methoxy-2H-pyrrol-5-yl)-6H-thieno[2,3-b]pyrrole;

(Z)-5-(2-((3,5-dimethyl-1H-pyrrol-2-yl)methylene)-3-methoxy-2H-pyrrol-5-yl)-2-methyl-6H-thieno[2,3-b]pyrrole;

(Z)-2-chloro-5-(2-((3,5-dimethyl-1H-pyrrol-2-yl)methylene)-3-methoxy-2H-pyrrol-5-yl)-6H-thieno[2,3-b]pyrrole;

(Z)-2-bromo-5-(2-((3,5-dimethyl-1H-pyrrol-2-yl)methylene)-3-methoxy-2H-pyrrol-5-yl)-6H-thieno[2,3-b]pyrrole;

(Z)-2-(5-(2-((3,5-dimethyl-1H-pyrrol-2-yl)methylene)-3-methoxy-2H-pyrrol-5-yl)-4H-thieno[3,2-b]pyrrol-2-yl)propan-2-ol;

(Z)-1-(5-(2-((3,5-dimethyl-1H-pyrrol-2-yl)methylene)-3-methoxy-2H-pyrrol-5-yl)-4H-thieno[3,2-b]pyrrol-2-yl)ethanol;

(Z)-1-(5-(2-((3,5-dimethyl-1H-pyrrol-2-yl)methylene)-3-methoxy-2H-pyrrol-5-yl)-4H-thieno[3,2-b]pyrrol-2-yl)ethanone;

(Z)-1-(5-(2-((3,5-dimethyl-1H-pyrrol-2-yl)methylene)-3-methoxy-2H-pyrrol-5-yl)-4H-thieno[3,2-b]pyrrol-2-yl)propan-1-one;

(Z)-1-(5-(2-((3,5-dimethyl-1H-pyrrol-2-yl)methylene)-3-methoxy-2H-pyrrol-5-yl)-4H-thieno[3,2-b]pyrrol-2-yl)-2-methylpropan-1-one;

(Z)-2-(5-(2-((3,5-dimethyl-1H-pyrrol-2-yl)methylene)-3-methoxy-2H-pyrrol-5-yl)-4H-thieno[3,2-b]pyrrol-2-yl)-1,1,1,3,3,3-hexafluoropropan-2-ol;

(Z)-1-(5-(2-((3,5-dimethyl-1H-pyrrol-2-yl)methylene)-3-methoxy-2H-pyrrol-5-yl)-4H-thieno[3,2-b]pyrrol-2-yl)-2,2,2-trifluoroethanol.

According to another embodiment, there is provided a prodrug of the compounds of the present invention.

According to another embodiment, the prodrug according to the present invention may have Formula IIIa or IIIb:

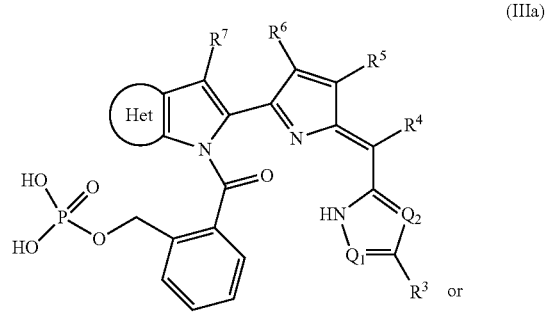

(IIIa)

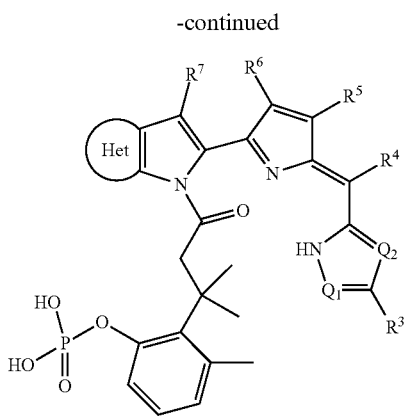
(IIIb)

or a pharmaceutically acceptable salt thereof.

According to another embodiment, there is provided a method of treating a patient with cancer of bladder, brain, breast, uterus, colon, esophagus, liver, ovary, prostate, a lymphoblastic leukemia, a follicular lymphomas, a melanomas, a malignant homeopathies, a myelomas, a chronic lymphoid leukemia, a non-small-cell lung cancers, a small-cell lung cancers, and a lymphoid malignancy of B-cell origin, with at least one of a compound of the present invention or a prodrug of the present invention.

According to another embodiment, there is provided a composition comprising at least one of a compound of the present invention or a prodrug of the present invention in combination with a pharmaceutically acceptable carrier.

According to another embodiment, there is provided a composition comprising at least one of a compound of the present invention or a prodrug of the present invention in combination with an anti-cancer agent chosen from a cytotoxic agent, an antimitotic agent, an anti-metabolite, a proteasome inhibitor, an HDAC inhibitor and a kinase inhibitor.

According to another embodiment, there is provided a method of treating a patient afflicted with cancer, comprising the step of administering to the patient a therapeutically effective amount of at least one of a compound of any one of claims 1-5 or a prodrug of any one of claims 6-7, in combination with radiotherapy.

According to another embodiment, there is provided a use of at least one of a compound of the present invention or a prodrug of the present invention for the preparation of a medicament for the treatment of a cancer.

According to another embodiment, there is provided a use of at least one of a compound of the present invention or a prodrug of the present invention for the treatment of a cancer.

According to another embodiment, there is provided a method of treating a patient afflicted with cancer, comprising the step of administering to the patient a therapeutically effective amount of a composition of the present invention, in combination with radiotherapy.

According to another embodiment, there is provided a use of a composition of the present invention for the preparation of a medicament for the treatment of a cancer.

According to another embodiment, there is provided a use of a composition of the present invention for the treatment of cancer.

The following terms are defined below.

Abbreviations used herein have their conventional meaning within the chemical and biological arts.

"alkyl," by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl". Alkyl groups are optionally substituted with one or more halogen atoms.

"Alkylene" by itself or as part of another substituent means a divalent radical derived from an alkyl, as exemplified, but not limited, by —$CH_2CH_2CH_2CH_2$—, —$CH_2CH$=$CHCH_2$—, —$CH_2C$≡$CCH_2$—, $CH_2CH_2CH(CH_2CH_2CH_3)CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each of which having from 3 to 10 carbon atoms. A "fused analog" of cycloalkyl means a monocyclic rings fused to an aryl or heteroaryl group in which the point of attachment is on the non-aromatic portion. Examples of cycloalkyl and fused analogs thereof include cyclopropyl, cyclobutyl, cyclopentyl, cyclohexyl, cycloheptyl, tetrahydronaphthyl, decahydronaphthyl, indanyl, and the like.

"Alkoxy" means alkoxy groups of a straight or branched having the indicated number of carbon atoms. $C_{1-6}$alkoxy, for example, includes methoxy, ethoxy, propoxy, isopropoxy, and the like.

"Heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR',
—SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cycloalkoxy" means cycloalkyl as defined above bonded to an oxygen atom, such as cyclopropyloxy.

"Fluoroalkoxy" means alkoxy as defined above wherein one or more hydrogen atoms have been replaced by fluoro atoms.

"Aryl" means mono- or bicyclic aromatic rings containing only carbon atoms. A "fused analog" of aryl means an aryl group fused to a monocyclic cycloalkyl or monocyclic heterocyclyl group in which the point of attachment is on the aromatic portion. Examples of aryl and fused analogs thereof include phenyl, naphthyl, indanyl, indenyl, tetrahydronaphthyl, 2,3-dihydrobenzofuranyl, dihydrobenzopyranyl, 1,4-benzodioxanyl, and the like.

"Heteroaryl" means a mono- or bicyclic aromatic ring containing at least one heteroatom selected from N, O and S, with each ring containing 5 to 6 atoms. A "fused analog" of heteroaryl means a heteroaryl group fused to a monocyclic cycloalkyl or monocyclic heterocyclyl group in which the point of attachment is on the aromatic portion. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo (2,3-b)pyridyl, quinolyl, indolyl, isoquinolyl, and the like.

The said aryl groups and said heteroaryl groups referred to in the definitions are unsubstituted or are substituted by at least one substituent selected from the group consisting of substituents a;

The said substituents α are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms, arylcarbonyl groups, two adjacent-x groups are optionally joined together to form an alkylene or an alkenylene chain having 3 or 4 carbon atoms, aminocarbonyl groups, alkenyl groups having from 2 to 5 carbon atoms, alkylthio groups having from 1 to 4 carbon atoms, aminosulfinyl groups, aminosulfonyl groups, hydroxy groups, hydroxyalkyl groups having from 1 to 4 carbon atoms, nitro groups, amino groups, carboxy groups, alkoxycarbonyl groups having from 2 to 5 carbon atoms, alkoxyalkyl groups having from 1 to 4 carbon atoms, alkylsulfonyl groups having from 1 to 4 carbon atoms, alkanoylamino groups having from 1 to 4 carbon atoms, alkanoyl(alkyl)amino groups having from 1 to 6 carbon atoms, alkanoylaminoalkyl groups having from 1 to 6 carbon atoms in both the alkanoyl and alkyl part, alkanoyl(alkyl)aminoalkyl groups having from 1 to 6 carbon atoms in both the alkanoyl and each alkyl part, alkylsulfonylamino groups having from 1 to 4 carbon atoms, mono- or di-alkylaminocarbonyl groups having from 1 to 6 carbon atoms, mono- or di-alkylaminosulfinyl groups having from 1 to 6 carbon atoms, mono- or di alkylaminosulfonyl groups having from 1 to 6 carbon atoms, aminoalkyl groups having from 1 to 4 carbon atoms, mono- or di-alkylamino groups having from 1 to 6 carbon atoms, mono- or di-alkylaminoalkyl groups having from 1 to 6 carbon atoms in each alkyl part, aralkyl groups having from 7 to 10 carbon atoms, heteroarylalkyl groups having from 1 to 4 carbon atoms in the alkyl part, heteroarylalkoxy groups having from 1 to 4 carbon atoms in the alkoxy part and alkylsulfonylamino groups having from 1 to 4 carbon atoms;

"Heterocyclyl" means mono- or bicyclic saturated rings containing at least one heteroatom selected from N, S and O, each of said ring having from 3 to 10 atoms in which the point of attachment may be carbon or nitrogen. A "fused analog" of heterocyclyl means a monocyclic heterocycle fused to an aryl or heteroaryl group in which the point of attachment is on the non-aromatic portion. Examples of "heterocyclyl" and fused analogs thereof include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

"halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrugs may also have improved solubility in pharmaceutical compositions over the parent drug. An example, without limitation, of a prodrug would be a compound of any of Formula I, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

DETAILED DESCRIPTION

In embodiments there is disclosed a genus of compounds of Formula I as apoptosis inducers

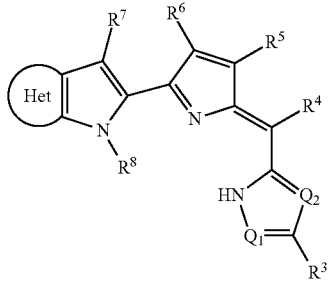

or a pharmaceutically acceptable salt thereof, wherein:
$Q_1$ is —C($R^1$)— or —N—;
$Q_2$ is —C($R^2$)— or —N—;
$R^1$, $R^2$, and $R^3$ are independently —$Y_m$($R_b$), wherein $R_b$ is —H, halogen, —$NH_2$, —CN, —$NO_2$, —SH, —$N_3$, —$C_1$-$C_8$ alkyl, —O—($C_1$-$C_8$ alkyl), —$C_2$-$C_8$ alkenyl, —$C_2$-$C_8$ alkynyl, —$C_3$-$C_{12}$ cycloalkyl, -aryl, -heteroaryl, -3- to 9-membered heterocycle, —$OR^9$, —O($CH_2$)$_n$$OR^9$, —C(O)$R^9$, —O—C(O)$R^9$, —C(O)($CH_2$)$_n$—$R^9$, —O—C(O)$OR^9$, —O—C(O)$NHR^9$, —O—C(O)N($R^9$)$_2$, —C(O)N($R^9$)$_2$, —C(O)$OR^9$, —C(O)$NHR^9$, —S—$R^9$, —S(O)$R^9$, —S(O)$_2$$R^9$, —NHC(O)$R^9$, —NHS(O)$_2$$R^9$, —O—C(S)$R^9$, —O—C(S)$OR^9$, —O—C(S)$NHR^9$, O—C(S)N($R^9$)$_2$, —C(S)$OR^9$, —C(S)$NHR^9$, —C(S)N($R^9$)$_2$, —NHC(S)$R^9$, —$NR^9$C(S)$R^9$, —NHC(S)$NHR^9$, —NHC(S)N($R^9$)$_2$, —$NR^9$C(S)$NHR^9$, —$NR^9$C(S)N($R^9$)$_2$ or $R^1$ and $R^3$, or $R^2$ and $R^3$, together with the carbon atom to which each is attached, join to form a 5- to 9-membered ring which is unsubstituted or substituted by 1 to 3 hetero atoms;
$R^4$ is —H, halogen, —OH, —$NH_2$, —$C_1$-$C_8$ alkyl, or —O—($C_1$-$C_8$ alkyl);
$R^5$ is —$Y_n$—($R_c$), wherein —$R_c$ is —$C_1$-$C_8$ alkyl, —O—($C_1$-$C_8$ alkyl), —O-benzyl, —OH, —$NH_2$, —NH($C_1$-$C_5$ alkyl), —N($C_1$-$C_5$ alkyl)$_2$, —NH(aryl), —N(aryl)$_2$, —NH(heteroaryl), —N(heteroaryl)$_2$, —CN, —$NO_2$, —$N_3$, —$C_2$-$C_8$ alkynyl, —$OR^9$, —O($CH_2$)$_n$$OR^9$, —C(O)$R_9$, —O—C(O)$R^9$, —C(O)($CH_2$)$_n$—$R^9$, —O—C(O)$OR^9$, —O—C(O)$NHR^9$, —O—C(O)N($R^9$)$_2$, —C(O)N($R^9$)$_2$, —C(O)$OR^9$, —C(O)$NHR^9$, —S—$R^9$, —S(O)$R^9$, —S(O)$_2$$R^9$, —NHC(O)$R^9$, —NHS(O)$_2$$R^9$, —O—C(S)$R^9$, —O—C(S)$OR^9$, —O—C(S)$NHR^9$, O—C(S)N($R^9$)$^2$, —C(S)$OR^9$, —C(S)$NHR^9$, —C(S)N($R^9$)2, —NHC(S)$R^9$, —$NR^9$C(S)$R^9$, —NHC(S)$NHR^9$, —NHC(S)N($R^9$)$_2$, —$NR^9$C(S)$NHR^9$, —$NR^9$C(S)N($R^9$)$_2$;
$R^6$ is —$Y_m$($R_d$), wherein —$R_d$ is —H, —OH, halogen, amino, -aryl, -heteroaryl, —NH($C_1$-$C_5$ alkyl), —N($C_1$-$C_8$ alkyl)$_2$, —NH(aryl), —N(aryl)$_2$, —NH(heteroaryl), —N(heteroaryl)$_2$, —CN, —$NO_2$, —$N_3$, —$C_1$-$C_8$ alkyl, —O—($C_1$-$C_8$ alkyl), —($C_1$-$C_8$ alkyl)-OH, —$C_2$-$C_8$ alkenyl, —$C_2$-$C_8$ alkynyl, —$C_3$-$C_{12}$ cycloalkyl, -aryl, -heteroaryl, -3- to 9-membered heterocycle, —$OR^9$, —O($CH_2$)$_n$$OR^9$, —C(O)$R^9$, —O—C(O)$R^9$, —C(O)($CH_2$)$_n$—$R^9$, —O—C(O)$OR^9$, —O—C(O)$NHR^9$, —O—C(O)N($R^9$)2, —C(O)N($R^9$)$_2$, —C(O)$OR^9$, —C(O)$NHR^9$, —S—$R^9$, —S(O)$R^9$, —S(O)$_2$$R^9$, —NHC(O)$R^9$, —NHS(O)$_2$$R^9$, —O—C(S)$R^9$, —O—C(S)$OR^9$, —O—C(S)$NHR^9$, O—C(S)N($R^9$)$_2$, —C(S)$OR^9$, —C(S)$NHR^9$, —C(S)N($R^9$)$_2$, —NHC(S)$R^9$, —$NR^9$C(S)$R^9$, —NHC(S)$NHR^9$, —NHC(S)N($R^9$)$_2$, —$NR^9$C(S)$NHR^9$, —$NR^9$C(S)N($R^9$)$_2$;

$R^7$ is —$Y_m$($R_e$), wherein —$R_e$ is —H, halogen, —$NH_2$, $C_1$-$C_8$ alkyl, -aryl, -heteroaryl, —NH($C_1$-$C_8$ alkyl), —N($C_1$-$C_8$ alkyl)$_2$, —NH(aryl), —N(aryl)$_2$, —NH(heteroaryl), —N(heteroaryl)$_2$, —C(O)NH($C_1$-$C_5$ alkyl), —C(O)N($C_1$-$C_5$ alkyl)$_2$, —NHC(O)($C_1$-$C_8$ alkyl), —NHC(=$NH2^+$)$NH_2$, —CN, —$NO_2$, $N_3$, -3- to 9-membered heterocycle, —$OR^9$, —O($CH_2$)$_n$$OR^9$, —C(O)$R^9$, —O—C(O)$R^9$, —C(O)($CH_2$)$_n$—$R^9$, —O—C(O)$OR^9$, —O—C(O)$NHR^9$, —O—C(O)N($R^9$)$_2$, —C(O)N($R^9$)$_2$, —C(O)$OR^9$, —C(O)$NHR^9$, —S—$R^9$, —S(O)$R^9$, —S(O)$_2$$R^9$, —NHC(O)$R^9$, —NHS(O)$_2$$R^9$, —O—C(S)$R_9$, —O—C(S)$OR^9$, —O—C(S)$NHR^9$, O—C(S)N($R^9$)$_2$, —C(S)$OR^9$, —C(S)$NHR^9$, —C(S)N($R^9$)$_2$, —NHC(S)$R^9$, —$NR^9$C(S)$R^9$, —NHC(S)$NHR^9$, —NHC(S)N($R^9$)$_2$, —$NR^9$C(S)$NHR^9$, —$NR^9$C(S)N($R^9$)$_2$;
$R^8$ is —$Y_m$($R_a$), wherein —$R_a$ is —H, —OH, —$C_1$-$C_8$ alkyl, —$C_2$-$C_8$ alkenyl, —$C_2$-$C_8$ alkynyl, $C_3$-$C_{12}$ cycloalkyl, -aryl, -heteroaryl, -3- to 9-membered heterocycle, —$OR^9$, —O($CH_2$)$_n$$OR^9$, —C(O)$R^9$, —O—C(O)$R^9$, —C(O)($CH_2$)$_n$—$R^9$, —O—C(O)$OR^9$, —O—C(O)$NHR^9$, —O—C(O)N($R^9$)$^2$, —C(O)N($R^9$)$_2$, —C(O)$OR^9$, —C(O)$NHR^9$, —S—$R^9$, —S(O)$R^9$, —S(O)$_2$$R^9$, —NHC(O)$R^9$, —NHS(O)$_2$$R^9$, —O—C(S)$R^9$, —O—C(S)$OR^9$, —O—C(S)$NHR^9$, O—C(S)N($R^9$)$_2$, —C(S)$OR^9$, —C(S)$NHR^9$, —C(S)N($R^9$)$_2$, —NHC(S)$R^9$, —$NR^9$C(S)$R^9$, —NHC(S)$NHR^9$, —NHC(S)N($R^9$)$_2$, —$NR^9$C(S)$NHR^9$, —$NR^9$C(S)N($R^9$)$_2$;
$R^9$ is independently —H, —$C_1$-$C_8$ alkyl, —$C_3$-$C_{12}$ cycloalkyl, -aryl, -heteroaryl, -3- to 9-membered heterocycle, —$C_2$-$C_8$ alkenyl, or —$C_2$-$C_8$ alkynyl;
wherein

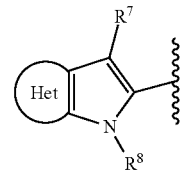

is selected from the from the following 6,5-bicyclic moieties:

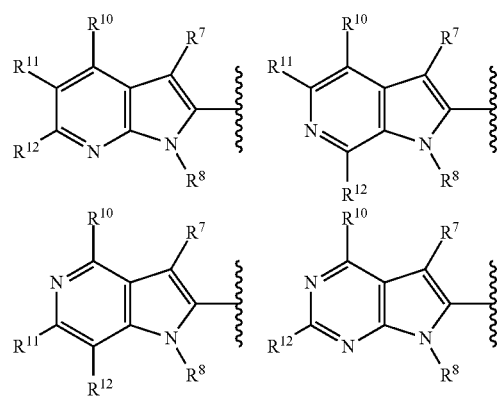

-continued

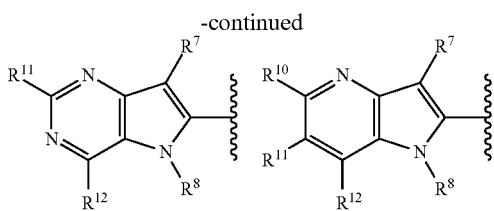

wherein
$R^{10}$, $R^{11}$ and $R^{12}$ are independently —$Y_m(R_f)$, wherein —$R_f$ is —H, halogen, —$NH_2$, $C_1$-$C_8$ alkyl, —$NH(C_1$-$C_5$ alkyl), —$N(C_1$-$C_5$ alkyl)$_2$, -aryl, -heteroaryl, —NH(aryl), —N(aryl)$_2$, —NH(heteroaryl), —N(heteroaryl)$_2$, —C(O)NH($C_1$-$C_5$ alkyl), —C(O)N($C_1$-$C_5$ alkyl)$_2$, —NHC(O)($C_1$-$C_5$ alkyl), —NHC(=$NH_2^+$)$NH_2$, —CN, —$NO_2$, $N_3$, -3- to 9-membered heterocycle, —$OR^9$, —O($CH_2)_nOR^9$, —C(OH)$R^9_2$, —CH(OH)$R^9$, —C(O)$R^9$, —O—C(O)$R^9$, —C(O)($CH_2)_n$—$R^9$, —O—C(O)$OR^9$, —O—C(O)$NHR^9$, —O—C(O)N($R^9)_2$, —C(O)N($R^9)_2$, —C(O)$OR^9$, —C(O)$NHR^9$, —S—$R^9$, —S(O)$R^9$, —S(O)$_2R^9$, —NHC(O)$R^9$, —NHS(O)$_2R^9$, —O—C(S)$R^9$, —O—C(S)$OR^9$, —O—C(S)$NHR^9$, O—C(S)N($R^9)_2$, —C(S)$OR^9$, —C(S)$NHR^9$, —C(S)N($R^9)_2$, —NHC(S)$R^9$, —$NR^9$C(S)$R^9$, —NHC(S)$NHR^9$, —NHC(S)N($R^9)_2$, —$NR^9$C(S)$NHR^9$, —$NR^9$C(S)N($R^9)_2$;
wherein when $R^{10}$ and $R^{11}$, or $R^{11}$ and $R^{12}$ are next to each other, together with the carbon atom to which each is attached, may join to form a 5- to 9-membered carbocycle or heterocycle;
each Y is independently $C_1$-$C_8$ alkylene-, —$C_2$-$C_8$ alkenylene- or —$C_2$-$C_8$ alkynylene-;
each m is independently 0 or 1; and
each n is independently an integer ranging from 0 to 6.

In another embodiment there is disclosed a genus of compounds of Formula II as apoptosis inducers

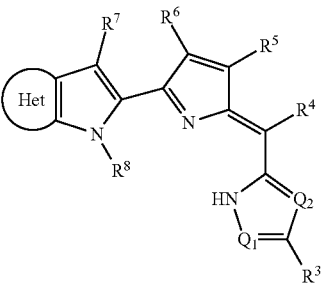

II or a pharmaceutically acceptable salt thereof, wherein:
$Q_1$ is C($R^1$)— or N—;
$Q_2$ is C($R^2$)— or N—;
$R^1$, $R^2$, and $R^3$ are independently —$Y_m(R_b)$, wherein $R_b$ is —H, halogen, —$NH_2$, —CN, —$NO_2$, —SH, —$N_3$, —$C_1$-$C_8$ alkyl, —O—($C_1$-$C_8$ alkyl), —$C_2$-$C_8$ alkenyl, —$C_2$-$C_8$ alkynyl, —$C_3$-$C_{12}$ cycloalkyl, -aryl, -heteroaryl, -3- to 9-membered heterocycle, —$OR^9$, —O($CH_2)_nOR^9$, —C(O)$R^9$, —O—C(O)$R^9$, —C(O)($CH_2)_n$—$R^9$, —O—C(O)$OR^9$, —O—C(O)$NHR^9$, —O—C(O)N($R^9)_2$, —C(O)N($R^9)_2$, —C(O)$OR^9$, —C(O)$NHR^9$, —S—$R^9$, —S(O)$R^9$, —S(O)$_2R^9$, —NHC(O)$R^9$, —NHS(O)$_2R^9$, —O—C(S)$R^9$, —O—C(S)$OR^9$, —O—C(S)$NHR^9$, O—C(S)N($R^9)_2$, —C(S)$OR^9$, —C(S)$NHR^9$, —C(S)N($R^9)_2$, —NHC(S)$R^9$, —$NR^9$C(S)$R^9$, —NHC(S)$NHR^9$, —NHC(S)N($R^9)_2$, —$NR^9$C(S)$NHR^9$, —$NR^9$C(S)N($R^9)_2$ or $R^1$ and $R^3$, or $R^2$ and $R^3$, together with the carbon atom to which each is attached, may join to form a 5- to 9-membered ring which is unsubstituted or substituted by 1 to 3 hetero atoms;
$R^4$ is —H, halogen, —OH, —$NH_2$, —$C_1$-$C_8$ alkyl, or —O—($C_1$-$C_8$ alkyl);
$R^5$ is —$Y_m$—($R_c$), wherein —$R_c$ is —$C_1$-$C_8$ alkyl, —O—($C_1$-$C_8$ alkyl), —O-benzyl, —OH, —$NH_2$, —NH($C_1$-$C_5$ alkyl), —N($C_1$-$C_5$ alkyl)$_2$, —NH(aryl), —N(aryl)$_2$, —NH(heteroaryl), —N(heteroaryl)$_2$, —CN, —$NO_2$, —$N_3$, —$C_2$-$C_8$ alkynyl, —$OR^9$, —O($CH_2)_nOR^9$, —C(O)$R_9$, —O—C(O)$R^9$, —C(O)($CH_2)_n$—$R^9$, —O—C(O)$OR^9$, —O—C(O)$NHR^9$, —O—C(O)N($R^9)_2$, —C(O)N($R^9)_2$, —C(O)$OR^9$, —C(O)$NHR^9$, —S—$R^9$, —S(O)$R^9$, —S(O)$_2R^9$, —NHC(O)$R^9$, —NHS(O)$_2R^9$, —O—C(S)$R^9$, —O—C(S)$OR^9$, —O—C(S)$NHR^9$, O—C(S)N($R^9)^2$, —C(S)$OR^9$, —C(S)$NHR^9$, —C(S)N($R^9)2$, —NHC(S)$R^9$, —$NR^9$C(S)$R^9$, —NHC(S)$NHR^9$, —NHC(S)N($R^9)_2$, —$NR^9$C(S)$NHR^9$, —$NR^9$C(S)N($R^9)_2$;
$R^6$ is —$Y_m(R_d)$, wherein —$R_d$ is —H, —OH, halogen, amino, -aryl, -heteroaryl, —NH($C_1$-$C_5$ alkyl), —N($C_1$-$C_5$ alkyl)$_2$, —NH(aryl), —N(aryl)$_2$, —NH(heteroaryl), —N(heteroaryl)$_2$, —CN, —$NO_2$, —$N_3$, —$C_1$-$C_8$ alkyl, —O—($C_1$-$C_8$ alkyl), —($C_1$-$C_8$ alkyl)-OH, —$C_2$-$C_8$ alkenyl, —$C_2$-$C_8$ alkynyl, —$C_3$-$C_{12}$ cycloalkyl, -aryl, -heteroaryl, -3- to 9-membered heterocycle, —$OR^9$, —O($CH_2)_nOR^9$, —C(O)$R^9$, —O—C(O)$R^9$, —C(O)($CH_2)_n$—$R^9$, —O—C(O)$OR^9$, —O—C(O)$NHR^9$, —O—C(O)N($R^9)2$, —C(O)N($R^9)_2$, —C(O)$OR^9$, —C(O)$NHR^9$, —S—$R^9$, —S(O)$R^9$, —S(O)$_2R^9$, —NHC(O)$R^9$, —NHS(O)$_2R^9$, —O—C(S)$R^9$, —O—C(S)$OR^9$, —O—C(S)$NHR^9$, O—C(S)N($R^9)_2$, —C(S)$OR^9$, —C(S)$NHR^9$, —C(S)N($R^9)_2$, —NHC(S)$R^9$, —$NR^9$C(S)$R^9$, —NHC(S)$NHR^9$, —NHC(S)N($R^9)_2$, —$NR^9$C(S)$NHR^9$, —$NR^9$C(S)N($R^9)_2$;
$R^7$ is —$Y_m(R_e)$, wherein —$R_e$ is —H, halogen, —$NH_2$, $C_1$-$C_8$ alkyl, -aryl, -heteroaryl, —NH($C_1$-$C_5$ alkyl), —N($C_1$-$C_5$ alkyl)$_2$, —NH(aryl), —N(aryl)$_2$, —NH(heteroaryl), —N(heteroaryl)$_2$, —C(O)NH($C_1$-$C_5$ alkyl), —C(O)N($C_1$-$C_5$ alkyl)$_2$, —NHC(O)($C_1$-$C_5$ alkyl), —NHC(=$NH2^+$)$NH_2$, —CN, —$NO_2$, $N_3$, -3- to 9-membered heterocycle, —$OR^9$, —O($CH_2)_nOR^9$, —C(O)$R^9$, —O—C(O)$R^9$, —C(O)($CH_2)_n$—$R^9$, —O—C(O)$OR^9$, —O—C(O)$NHR^9$, —O—C(O)N($R^9)_2$, —C(O)N($R^9)_2$, —C(O)$OR^9$, —C(O)$NHR^9$, —S—$R^9$, —S(O)$R^9$, —S(O)$_2R^9$, —NHC(O)$R^9$, —NHS(O)$_2R^9$, —O—C(S)$R_9$, —O—C(S)$OR^9$, —O—C(S)$NHR^9$, O—C(S)N($R^9)_2$, —C(S)$OR^9$, —C(S)$NHR^9$, —C(S)N($R^9)_2$, —NHC(S)$R^9$, —$NR^9$C(S)$R^9$, —NHC(S)$NHR^9$, —NHC(S)N($R^9)_2$, —$NR^9$C(S)$NHR^9$, —$NR^9$C(S)N($R^9)_2$;
$R^8$ is —$Y_m(R_a)$, wherein —$R_a$ is —H, —OH, —$C_1$-$C_8$ alkyl, —$C_2$-$C_8$ alkenyl, —$C_2$-$C_8$ alkynyl, $C_3$-$C_{12}$ cycloalkyl, -aryl, -heteroaryl, -3- to 9-membered heterocycle, —$OR^9$, —O($CH_2)_nOR^9$, —C(O)$R^9$, —O—C(O)$R^9$, —C(O)($CH_2)_n$—$R^9$, —O—C(O)$OR^9$, —O—C(O)$NHR^9$, —O—C(O)N($R^9)^2$, —C(O)N($R^9)_2$, —C(O)$OR^9$, —C(O)$NHR^9$, —S—$R^9$, —S(O)$R^9$, —S(O)$_2R^9$, —NHC(O)$R^9$, —NHS(O)$_2R^9$, —O—C(S)$R^9$, —O—C(S)$OR^9$, —O—C(S)$NHR^9$, O—C(S)N($R^9)_2$, —C(S)$OR^9$, —C(S)$NHR^9$, —C(S)N($R^9)_2$, —NHC(S)$R^9$, —$NR^9$C(S)$R^9$, —NHC(S)$NHR^9$, —NHC(S)N($R^9)_2$, —$NR^9$C(S)$NHR^9$, —$NR^9$C(S)N($R^9)_2$;
$R^9$ is independently —H, —$C_1$-$C_8$ alkyl, —$C_3$-$C_{12}$ cycloalkyl, -aryl, -heteroaryl, -3- to 9-membered heterocycle, —$C_2$-$C_8$ alkenyl, or —$C_2$-$C_8$ alkynyl;

wherein

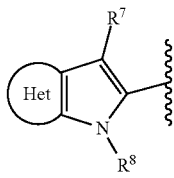

is selected from the from the following 5,5-bicyclic moieties:

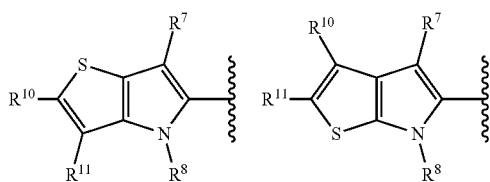

wherein
$R^{10}$, and $R^{11}$ are independently —$Y_m(R_f)$, wherein —$R_f$ is —H, halogen, —$NH_2$, $C_1$-$C_8$ alkyl, —$NH(C_1$-$C_5$ alkyl), —$N(C_1$-$C_5$ alkyl)$_2$, -aryl, -heteroaryl, —NH(aryl), —N(aryl)$_2$, —NH(heteroaryl), —N(heteroaryl)$_2$, —C(O)NH($C_1$-$C_8$ alkyl), —C(O)N($C_1$-$C_8$ alkyl)$_2$, —NHC(O)($C_1$-$C_8$ alkyl), —NHC(=$NH_2^+$)$NH_2$, —CN, —$NO_2$, $N_3$, -3- to 9-membered heterocycle, —$OR^9$, —O($CH_2$)$_n OR^9$, —C(OH)$R^9{}_2$, —CH(OH)$R^9$, —C(O)$R^9$, —O—C(O)$R^9$, —C(O)($CH_2$)$_n$—$R^9$, —O—C(O)$OR^9$, —O—C(O)$NHR^9$, —O—C(O)N($R^9$)$_2$, —C(O)N($R^9$)$_2$, —C(O)$OR^9$, —C(O)$NHR^9$, —S—$R^9$, —S(O)$R^9$, —S(O)$_2R^9$, —NHC(O)$R^9$, —NHS(O)$_2R^9$, —O—C(S)$R^9$, —O—C(S)$OR^9$, —O—C(S)$NHR^9$, O—C(S)N($R^9$)$_2$, —C(S)$OR^9$, —C(S)$NHR^9$, —C(S)N($R^9$)$_2$, —NHC(S)$R^9$, —$NR^9$C(S)$R^9$, —NHC(S)$NHR^9$, —NHC(S)N($R^9$)$_2$, —$NR^9$C(S)$NHR^9$, —$NR^9$C(S)N($R^9$)$_2$;
wherein when $R^{10}$ and $R^{11}$ together with the carbon atom to which each is attached, may join to form a 5- to 9-membered carbocycle or heterocycle;
each Y is independently —$C_1$-$C_8$ alkylene-, —$C_2$-$C_8$ alkenylene- or —$C_2$-$C_8$ alkynylene-;
each m is independently 0 or 1; and
each n is independently an integer ranging from 0 to 6.

In another embodiment there is disclosed a genus of compounds of Formula IIa as apoptosis inducers

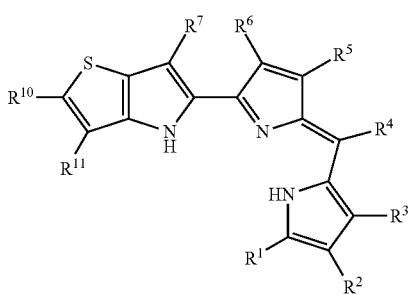

IIa or a pharmaceutically acceptable salt thereof, wherein:
$R^1$, $R^2$, and $R^3$ are independently —$Y_m(R_b)$, wherein $R_b$ is —H, halogen, —$NH_2$, —CN, —$NO_2$, —SH, —$N_3$, —$C_1$-$C_8$ alkyl, —O—($C_1$-$C_8$ alkyl), —$C_2$-$C_8$ alkenyl, —$C_2$-$C_8$ alkynyl, —$C_3$-$C_{12}$ cycloalkyl, -aryl, -heteroaryl, -3- to 9-membered heterocycle, —$OR^9$, —O($CH_2$)$_nOR^9$, —C(O)$R^9$, —O—C(O)$R^9$, —C(O)($CH_2$)$_n$—$R^9$, —O—C(O)$OR^9$, —O—C(O)$NHR^9$, —O—C(O)N($R^9$)$_2$, —C(O)N($R^9$)$_2$, —C(O)$OR^9$, —C(O)$NHR^9$, —S—$R^9$, —S(O)$R^9$, —S(O)$_2R^9$, —NHC(O)$R^9$, —NHS(O)$_2R^9$, —O—C(S)$R^9$, —O—C(S)$OR^9$, —O—C(S)$NHR^9$, O—C(S)N($R^9$)$_2$, —C(S)$OR^9$, —C(S)$NHR^9$, —C(S)N($R^9$)$_2$, —NHC(S)$R^9$, —$NR^9$C(S)$R^9$, —NHC(S)$NHR^9$, —NHC(S)N($R^9$)$_2$, —$NR^9$C(S)$NHR^9$, —$NR^9$C(S)N($R^9$)$_2$ or $R^1$ and $R^3$, or $R^2$ and $R^3$, together with the carbon atom to which each is attached, may join to form a 5- to 9-membered ring which is unsubstituted or substituted by 1 to 3 hetero atoms,
$R^4$ is —H, halogen, —OH, —$NH_2$, —$C_1$-$C_8$ alkyl, or —O—($C_1$-$C_8$ alkyl);
$R^5$ is —$Y_m$—($R_c$), wherein —$R_c$ is —$C_1$-$C_8$ alkyl, —O—($C_1$-$C_8$ alkyl), —O-benzyl, —OH, —$NH_2$, —NH($C_1$-$C_5$ alkyl), —N($C_1$-$C_5$ alkyl)$_2$, —NH(aryl), —N(aryl)$_2$, —NH(heteroaryl), —N(heteroaryl)$_2$, —CN, —$NO_2$, —$N_3$, —$C_2$-$C_8$ alkynyl, —$OR^9$, —O($CH_2$)$_nOR^9$, —C(O)$R_9$, —O—C(O)$R^9$, —C(O)($CH_2$)$_n$—$R^9$, —O—C(O)$OR^9$, —O—C(O)$NHR^9$, —O—C(O)N($R^9$)$_2$, —C(O)N($R^9$)$_2$, —C(O)$OR^9$, —C(O)$NHR^9$, —S—$R^9$, —S(O)$R^9$, —S(O)$_2R^9$, —NHC(O)$R^9$, —NHS(O)$_2R^9$, —O—C(S)$R^9$, —O—C(S)$OR^9$, —O—C(S)$NHR^9$, O—C(S)N($R^9$)$^2$, —C(S)$OR^9$, —C(S)$NHR^9$, —C(S)N($R^9$)2, —NHC(S)$R^9$, —$NR^9$C(S)$R^9$, —NHC(S)$NHR^9$, —NHC(S)N($R^9$)$_2$, —$NR^9$C(S)$NHR^9$, —$NR^9$C(S)N($R^9$)$_2$;
$R^6$ is —$Y_m(R_d)$, wherein —$R_d$ is —H, —OH, halogen, amino, -aryl, -heteroaryl, $C_5$ alkyl), —N($C_1$-$C_5$ alkyl)$_2$, —NH(aryl), —N(aryl)$_2$, —NH(heteroaryl), —N(heteroaryl)$_2$, —CN, —$NO_2$, —$N_3$, —$C_1$-$C_8$ alkyl, —O—($C_1$-$C_8$ alkyl), —($C_1$-$C_8$ alkyl)-OH, —$C_2$-$C_8$ alkenyl, —$C_2$-$C_8$ alkynyl, —$C_3$-$C_{12}$ cycloalkyl, -aryl, heteroaryl, -3- to 9-membered heterocycle, —$OR^9$, —O($CH_2$)$_nOR^9$, —C(O)$R^9$, —O—C(O)$R^9$, —C(O)($CH_2$)$_n$—$R^9$, —O—C(O)$OR^9$, —O—C(O)$NHR^9$, —O—C(O)N($R^9$)2, —C(O)N($R^9$)$_2$, —C(O)$OR^9$, —C(O)$NHR^9$, —S—$R^9$, —S(O)$R^9$, —S(O)$_2R^9$, —NHC(O)$R^9$, —NHS(O)$_2R^9$, —O—C(S)$R^9$, —O—C(S)$OR^9$, —O—C(S)$NHR^9$, O—C(S)N($R^9$)$_2$, —C(S)$OR^9$, —C(S)$NHR^9$, —C(S)N($R^9$)$_2$, —NHC(S)$R^9$, —$NR^9$C(S)$R^9$, —NHC(S)$NHR^9$, —NHC(S)N($R^9$)$_2$, —$NR^9$C(S)$NHR^9$, —$NR^9$C(S)N($R^9$)$_2$;
$R^7$ is —$Y_m(R_e)$, wherein —$R_e$ is —H, halogen, —$NH_2$, $C_1$-$C_8$ alkyl, -aryl, -heteroaryl, —NH($C_1$-$C_5$ alkyl), —N($C_1$-$C_5$ alkyl)$_2$, —NH(aryl), —N(aryl)$_2$, —NH(heteroaryl), —N(heteroaryl)$_2$, —C(O)NH($C_1$-$C_5$ alkyl), —C(O)N($C_1$-$C_5$ alkyl)$_2$, —NHC(O)($C_1$-$C_5$ alkyl), —NHC(=$NH2^+$)$NH_2$, —CN, —$NO_2$, $N_3$, -3- to 9-membered heterocycle, —$OR^9$, —O($CH_2$)$_nOR^9$, —C(O)$R^9$, —O—C(O)$R^9$, —C(O)($CH_2$)$_n$—$R^9$, —O—C(O)$OR^9$, —O—C(O)$NHR^9$, —O—C(O)N($R^9$)$_2$, —C(O)N($R^9$)$_2$, —C(O)$OR^9$, —C(O)$NHR^9$, —S—$R^9$, —S(O)$R^9$, —S(O)$_2R^9$, —NHC(O)$R^9$, —NHS(O)$_2R^9$, —O—C(S)$R_9$, —O—C(S)$OR^9$, —O—C(S)$NHR^9$, O—C(S)N($R^9$)$_2$, —C(S)$OR^9$, —C(S)$NHR^9$, —C(S)N($R^9$)$_2$, —NHC(S)$R^9$, —$NR^9$C(S)$R^9$, —NHC(S)$NHR^9$, —NHC(S)N($R^9$)$_2$, —$NR^9$C(S)$NHR^9$, —$NR^9$C(S)N($R^9$)$_2$;
$R^9$ is independently —H, —$C_1$-$C_8$ alkyl, —$C_1$-$C_8$ halogenated-alkyl, —$C_3$-$C_{12}$ cycloalkyl, -aryl, -heteroaryl, -3- to 9-membered heterocycle, —$C_2$-$C_8$ alkenyl, or —$C_2$-$C_8$ alkynyl;
$R^{10}$, and $R^{11}$ are independently —$Y_m(R_f)$, wherein —$R_f$ is —H, halogen, —$NH_2$, —$C_1$-$C_8$ alkyl, —NH($C_1$-$C_5$ alkyl), —N($C_1$-$C_5$ alkyl)$_2$, -aryl, -heteroaryl, —NH(aryl), —N(aryl)$_2$, —NH(heteroaryl), —N(heteroaryl)$_2$, —C(O)NH($C_1$-$C_5$ alkyl), —C(O)N($C_1$-$C_5$ alkyl)$_2$, —NHC(O)

($C_1$-$C_5$ alkyl), —NHC(=$NH_2^+$)$NH_2$, —CN, —$NO_2$, $N_3$, -3- to 9-membered heterocycle, —$OR^9$, —O($CH_2$)$_n$$OR^9$, —C(OH)$R^9_2$, —CH(OH)$R^9$, —C(O)$R^9$, —O—C(O)$R^9$, —C(O)($CH_2$)$_n$—$R^9$, —O—C(O)$OR^9$, —O—C(O)$NHR^9$, —O—C(O)N($R^9$)$_2$, —C(O)N($R^9$)$_2$, —C(O)$OR^9$, —C(O)$NHR^9$, —S—$R^9$, —S(O)$R^9$, —S(O)$_2$$R^9$, —NHC(O)$R^9$, —NHS(O)$_2$$R^9$, —O—C(S)$R^9$, —O—C(S)$OR^9$, —O—C(S)$NHR^9$, O—C(S)N($R^9$)$_2$, —C(S)$OR^9$, —C(S)$NHR^9$, —C(S)N($R^9$)$_2$, —NHC(S)$R^9$, —$NR^9$C(S)$R^9$, —NHC(S)$NHR^9$, —NHC(S)N($R^9$)$_2$, —$NR^9$C(S)$NHR^9$, —$NR^9$C(S)N($R^9$)$_2$;

$R^{10}$ and $R^{11}$, together with the carbon atom to which each is attached, can form a 5- to 9-membered carbocycle or heterocycle;

each Y is independently —$C_1$-$C_8$ alkylene-, —$C_2$-$C_8$ alkenylene- or —$C_2$-$C_8$ alkynylene-;

each m is independently 0 or 1; and each n is independently an integer ranging from 0 to 6.

In another embodiment there is disclosed a genus of compounds of Formula IIb as apoptosis inducers

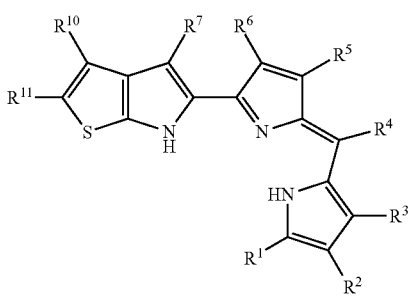

IIb or a pharmaceutically acceptable salt thereof, wherein:

$R^1$, $R^2$, and $R^3$ are independently —$Y_m$($R_b$), wherein $R_b$ is —H, halogen, —$NH_2$, —CN, —$NO_2$, —SH, —$N_3$, —$C_1$-$C_8$ alkyl, —O—($C_1$-$C_8$ alkyl), —$C_2$-$C_8$ alkenyl, —$C_2$-$C_8$ alkynyl, —$C_3$-$C_{12}$ cycloalkyl, -aryl, -heteroaryl, -3- to 9-membered heterocycle, —$OR^9$, —O($CH_2$)$_n$$OR^9$, —C(O)$R^9$, —O—C(O)$R^9$, —C(O)($CH_2$)$_n$—$R^9$, —O—C(O)$OR^9$, —O—C(O)$NHR^9$, —O—C(O)N($R^9$)$_2$, —C(O)N($R^9$)$_2$, —C(O)$OR^9$, —C(O)$NHR^9$, —S—$R^9$, —S(O)$R^9$, —S(O)$_2$$R^9$, —NHC(O)$R^9$, —NHS(O)$_2$$R^9$, —O—C(S)$R^9$, —O—C(S)$OR^9$, —O—C(S)$NHR^9$, O—C(S)N($R^9$)$_2$, —C(S)$OR^9$, —C(S)$NHR^9$, —C(S)N($R^9$)$_2$, —NHC(S)$R^9$, —$NR^9$C(S)$R^9$, —NHC(S)$NHR^9$, —NHC(S)N($R^9$)$_2$, —$NR^9$C(S)$NHR^9$, —$NR^9$C(S)N($R^9$)$_2$ or $R^1$ and $R^3$, or $R^2$ and $R^3$, together with the carbon atom to which each is attached, join to form a 5- to 9-membered ring which is unsubstituted or substituted by 1 to 3 hetero atoms, $R^4$ is —H, halogen, —OH, —$NH_2$, —$C_1$-$C_8$ alkyl, or —O—($C_1$-$C_8$ alkyl);

$R^5$ is —$Y_m$—($R_c$), wherein —$R_c$ is —$C_1$-$C_8$ alkyl, —O—($C_1$-$C_8$ alkyl), —O-benzyl, —OH, —$NH_2$, —NH($C_1$-$C_5$ alkyl), —N($C_1$-$C_5$ alkyl)$_2$, —NH(aryl), —N(aryl)$_2$, —NH(heteroaryl), —N(heteroaryl)$_2$, —CN, —$NO_2$, —$N_3$, —$C_2$-$C_8$ alkynyl, —$OR^9$, —O($CH_2$)$_n$$OR^9$, —C(O)$R_9$, —O—C(O)$R^9$, —C(O)($CH_2$)$_n$—$R^9$, —O—C(O)$OR^9$, —O—C(O)$NHR^9$, —O—C(O)N($R^9$)$_2$, —C(O)N($R^9$)$_2$, —C(O)$OR^9$, —C(O)$NHR^9$, —S—$R^9$, —S(O)$R^9$, —S(O)$_2$$R^9$, —NHC(O)$R^9$, —NHS(O)$_2$$R^9$, —O—C(S)$R^9$, —O—C(S)$OR^9$, —O—C(S)$NHR^9$, O—C(S)N($R^9$)$_2$, —C(S)$OR^9$, —C(S)$NHR^9$, —C(S)N($R^9$)2, —NHC(S)$R^9$, —$NR^9$C(S)$R^9$, —NHC(S)$NHR^9$, —NHC(S)N($R^9$)$_2$, —$NR^9$C(S)$NHR^9$, —$NR^9$C(S)N($R^9$)$_2$;

$R^6$ is —$Y_m$($R_d$), wherein —$R_d$ is —H, —OH, halogen, amino, -aryl, -heteroaryl, —NH($C_1$-$C_5$ alkyl), —N($C_1$-$C_5$ alkyl)$_2$, —NH(aryl), —N(aryl)$_2$, —NH(heteroaryl), —N(heteroaryl)$_2$, —CN, —$NO_2$, —$N_3$, —$C_1$-$C_8$ alkyl, —O—($C_1$-$C_8$ alkyl), —($C_1$-$C_8$ alkyl)-OH, —$C_2$-$C_8$ alkenyl, —$C_2$-$C_8$ alkynyl, —$C_3$-$C_{12}$ cycloalkyl, -aryl, -heteroaryl, -3- to 9-membered heterocycle, —$OR^9$, —O($CH_2$)$_n$$OR^9$, —C(O)$R^9$, —O—C(O)$R^9$, —C(O)($CH_2$)$_n$—$R^9$, —O—C(O)$OR^9$, —O—C(O)$NHR^9$, —O—C(O)N($R^9$)2, —C(O)N($R^9$)$_2$, —C(O)$OR^9$, —C(O)$NHR^9$, —S—$R^9$, —S(O)$R^9$, —S(O)$_2$$R^9$, —NHC(O)$R^9$, —NHS(O)$_2$$R^9$, —O—C(S)$R^9$, —O—C(S)$OR^9$, —O—C(S)$NHR^9$, O—C(S)N($R^9$)$_2$, —C(S)$OR^9$, —C(S)$NHR^9$, —C(S)N($R^9$)$_2$, —NHC(S)$R^9$, —$NR^9$C(S)$R^9$, —NHC(S)$NHR^9$, —NHC(S)N($R^9$)$_2$, —$NR^9$C(S)$NHR^9$, —$NR^9$C(S)N($R^9$)$_2$;

$R^7$ is —$Y_m$($R_e$), wherein —$R_e$ is —H, halogen, —$NH_2$, $C_1$-$C_8$ alkyl, -aryl, -heteroaryl, —NH($C_1$-$C_8$ alkyl), —N($C_1$-$C_5$ alkyl)$_2$, —NH(aryl), —N(aryl)$_2$, —NH(heteroaryl), —N(heteroaryl)$_2$, —C(O)NH($C_1$-$C_5$ alkyl), —C(O)N($C_1$-$C_8$ alkyl)$_2$, —NHC(O)($C_1$-$C_8$ alkyl), —NHC(=$NH_2^+$)$NH_2$, —CN, —$NO_2$, $N_3$, -3- to 9-membered heterocycle, —$OR^9$, —O($CH_2$)$_n$$OR^9$, —C(O)$R^9$, —O—C(O)$R^9$, —C(O)($CH_2$)$_n$—$R^9$, —O—C(O)$OR^9$, —O—C(O)$NHR^9$, —O—C(O)N($R^9$)$_2$, —C(O)N($R^9$)$_2$, —C(O)$OR^9$, —C(O)$NHR^9$, —S—$R^9$, —S(O)$R^9$, —S(O)$_2$$R^9$, —NHC(O)$R^9$, —NHS(O)$_2$$R^9$, —O—C(S)$R_9$, —O—C(S)$OR^9$, —O—C(S)$NHR^9$, —O—C(S)N($R^9$)$_2$, —C(S)$OR^9$, —C(S)$NHR^9$, —C(S)N($R^9$)$_2$, —NHC(S)$R^9$, —$NR^9$C(S)$R^9$, —NHC(S)$NHR^9$, —NHC(S)N($R^9$)$_2$, —$NR^9$C(S)$NHR^9$, —$NR^9$C(S)N($R^9$)$_2$;

$R^9$ is independently —H, —$C_1$-$C_8$ alkyl, —$C_3$-$C_{12}$ cycloalkyl, —$C_1$-$C_8$ halogenated-alkyl, -aryl, -heteroaryl, -3- to 9-membered heterocycle, —$C_2$-$C_8$ alkenyl, or —$C_2$-$C_8$ alkynyl;

$R^{10}$, and $R^{11}$ are independently —$Y_m$($R_f$), wherein —$R_f$ is —H, halogen, —$NH_2$, $C_1$-$C_8$ alkyl, —NH($C_1$-$C_8$ alkyl), —N($C_1$-$C_8$ alkyl)$_2$, -aryl, -heteroaryl, —NH(aryl), —N(aryl)$_2$, —NH(heteroaryl), —N(heteroaryl)$_2$, —C(O)NH($C_1$-$C_8$ alkyl), —C(O)N($C_1$-$C_8$ alkyl)$_2$, —NHC(O)($C_1$-$C_8$ alkyl), —NHC(=$NH_2^+$)$NH_2$, —CN, —$NO_2$, $N_3$, -3- to 9-membered heterocycle, —$OR^9$, —O($CH_2$)$_n$$OR^9$, —C(OH)$R^9_2$, —CH(OH)$R^9$, —C(O)$R^9$, —O—C(O)$R^9$, —C(O)($CH_2$)$_n$—$R^9$, —O—C(O)$OR^9$, —O—C(O)$NHR^9$, —O—C(O)N($R^9$)$_2$, —C(O)N($R^9$)$_2$, —C(O)$OR^9$, —C(O)$NHR^9$, —S—$R^9$, —S(O)$R^9$, —S(O)$_2$$R^9$, —NHC(O)$R^9$, —NHS(O)$_2$$R^9$, —O—C(S)$R^9$, —O—C(S)$OR^9$, —O—C(S)$NHR^9$, O—C(S)N($R^9$)$_2$, —C(S)$OR^9$, —C(S)$NHR^9$, —C(S)N($R^9$)$_2$, —NHC(S)$R^9$, —$NR^9$C(S)$R^9$, —NHC(S)$NHR^9$, —NHC(S)N($R^9$)$_2$, —$NR^9$C(S)$NHR^9$, —$NR^9$C(S)N($R^9$)$_2$;

$R^{10}$ and $R^{11}$, together with the carbon atom to which each is attached, can form a 5- to 9-membered carbocycle or heterocycle;

each Y is independently —$C_1$-$C_8$ alkylene-, —$C_2$-$C_8$ alkenylene- or —$C_2$-$C_8$ alkynylene-;

each m is independently 0 or 1; and each n is independently an integer ranging from 0 to 6.

Another embodiment comprises prodrugs of compounds having Formula I. For example, $R^8$ in Formula I can be selected from the following moieties:

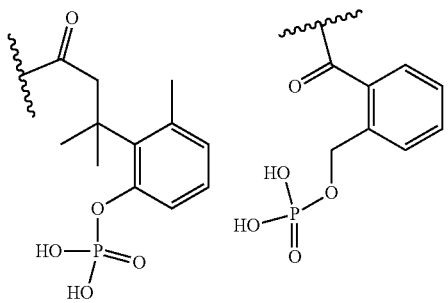

or a pharmaceutically acceptable salt thereof.

In another embodiment, the invention provides stable isotope-labeled analogs of Formula I.

More specifically, the invention relates to compounds of Formula I which are:

(Z)-2-(2-((3,5-dimethyl-1H-pyrrol-2-yl)methylene)-3-methoxy-2H-pyrrol-5-yl)-1H-pyrrolo[2,3-b]pyridine;

(Z)-2-(2-((3,5-dimethyl-1H-pyrrol-2-yl)methylene)-3-methoxy-2H-pyrrol-5-yl)-1H-pyrrolo[2,3-c]pyridine;

(Z)-2-(2-((3,5-dimethyl-1H-pyrrol-2-yl)methylene)-3-methoxy-2H-pyrrol-5-yl)-1H-pyrrolo[3,2-c]pyridine;

(Z)-2-(2-((3,5-dimethyl-1H-pyrrol-2-yl)methylene)-3-methoxy-2H-pyrrol-5-yl)-1H-pyrrolo[3,2-b]pyridine;

(Z)-5-(2-((3,5-dimethyl-1H-pyrrol-2-yl)methylene)-3-methoxy-2H-pyrrol-5-yl)-4H-thieno[3,2-b]pyrrole (Z)-2-chloro-5-(2-((3,5-dimethyl-1H-pyrrol-2-yl)methylene)-3-methoxy-2H-pyrrol-5-yl)-4H-thieno[3,2-b]pyrrole;

(Z)-5-(2-((3,5-dimethyl-1H-pyrrol-2-yl)methylene)-3-methoxy-2H-pyrrol-5-yl)-2-methyl-4H-thieno[3,2-b]pyrrole;

(Z)-2-bromo-5-(2-((3,5-dimethyl-1H-pyrrol-2-yl)methylene)-3-methoxy-2H-pyrrol-5-yl)-4H-thieno[3,2-b]pyrrole;

(Z)-5-(2-((3,5-dimethyl-1H-pyrrol-2-yl)methylene)-3-methoxy-2H-pyrrol-5-yl)-6H-thieno[2,3-b]pyrrole;

(Z)-5-(2-((3,5-dimethyl-1H-pyrrol-2-yl)methylene)-3-methoxy-2H-pyrrol-5-yl)-2-methyl-6H-thieno[2,3-b]pyrrole;

(Z)-2-chloro-5-(2-((3,5-dimethyl-1H-pyrrol-2-yl)methylene)-3-methoxy-2H-pyrrol-5-yl)-6H-thieno[2,3-b]pyrrole;

(Z)-2-bromo-5-(2-((3,5-dimethyl-1H-pyrrol-2-yl)methylene)-3-methoxy-2H-pyrrol-5-yl)-6H-thieno[2,3-b]pyrrole;

(Z)-2-(5-(2-((3,5-dimethyl-1H-pyrrol-2-yl)methylene)-3-methoxy-2H-pyrrol-5-yl)-4H-thieno[3,2-b]pyrrol-2-yl)propan-2-ol;

(Z)-1-(5-(2-((3,5-dimethyl-1H-pyrrol-2-yl)methylene)-3-methoxy-2H-pyrrol-5-yl)-4H-thieno[3,2-b]pyrrol-2-yl)ethanol;

(Z)-1-(5-(2-((3,5-dimethyl-1H-pyrrol-2-yl)methylene)-3-methoxy-2H-pyrrol-5-yl)-4H-thieno[3,2-b]pyrrol-2-yl)ethanone;

(Z)-1-(5-(2-((3,5-dimethyl-1H-pyrrol-2-yl)methylene)-3-methoxy-2H-pyrrol-5-yl)-4H-thieno[3,2-b]pyrrol-2-yl)propan-1-one;

(Z)-1-(5-(2-((3,5-dimethyl-1H-pyrrol-2-yl)methylene)-3-methoxy-2H-pyrrol-5-yl)-4H-thieno[3,2-b]pyrrol-2-yl)-2-methylpropan-1-one;

(Z)-2-(5-(2-((3,5-dimethyl-1H-pyrrol-2-yl)methylene)-3-methoxy-2H-pyrrol-5-yl)-4H-thieno[3,2-b]pyrrol-2-yl)-1,1,1,3,3,3-hexafluoropropan-2-ol;

(Z)-1-(5-(2-((3,5-dimethyl-1H-pyrrol-2-yl)methylene)-3-methoxy-2H-pyrrol-5-yl)-4H-thieno[3,2-b]pyrrol-2-yl)-2,2,2-trifluoroethanol.

Optical Isomers—Diastereomers—Geometric Isomers Tautomers

Compounds of Formula I, II or III contain one or more asymmetric centers and can thus occur as racemates and racemic mixtures, single enantiomers, diastereomeric mixtures and individual diastereomers. The present invention is meant to comprehend all such isomeric forms of the compounds of Formula I, II or III.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I, II or III may be separated into diastereoisomeric pairs of enantiomers by, for example, fractional crystallization from a suitable solvent, for example MeOH or EtOAc or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I may be obtained by stereospecific synthesis using optically pure starting materials or reagents of known configuration.

Stable Isotope-Labeled Analogs:

One or more than one of the protons in compounds of Formula I, II or III can be replaced with deuterium atom(s), thus providing deuterated analogs that may have improved pharmacological activities.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I, II or III are meant to also include the pharmaceutically acceptable salts.

It will be understood that, as used herein, references to the compounds of Formula I, II or III are meant to also include the pharmaceutically acceptable salts.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, preservative and flavoring and coloring agent. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an I atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns).

This may be achieved by any appropriate comminuting method, such as spiral jet milling, fluid bed jet milling, and supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from log to 20 mg of the compound of the invention per actuation and the actuation volume may vary from 11 to 100 l. A typical formulation may comprise a compound of Formula I, II or III, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 fig to 10 mg of the compound of Formula I, II or III. The overall daily dose will typically be in the range 1 lag to 10 mg which may be administered in a single dose or, more usually, as divided doses throughout the day.

Compounds of Formula I, II or III may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I, II or III are employed. (For purposes of this application, topical application shall include mouth washes and gargles.)

Dosage levels of the order of from about 0.01 mg to about 140 mg/kg of body weight per day are useful in the treatment of the above-indicated conditions, or alternatively about 0.5 mg to about 7 g per patient per day. For example, the cancer may be effectively treated by the administration of from about 0.01 to 50 mg of the compound per kilogram of body weight per day, or alternatively about 0.5 mg to about 3.5 g per patient per day, preferably 2.5 mg to 1 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Utilities

The compounds of the present invention are useful for treating diseases during which are expressed one or more than one of antiapoptotic Bcl-$x_L$ protein, antiapoptotic Bcl-2 protein or antiapoptotic Bcl-w protein, said compositions comprising an excipient and a therapeutically effective amount of the compound having Formula I, II or III.

The present invention also comprises methods of treating diseases in a patient during which are expressed one or more than one of antiapoptotic Bcl-$x_L$ protein, antiapoptotic Bcl-2 protein, antiapoptotic Bcl-w protein and Mcl-1 protein, said methods comprising administering to the patient a therapeutically effective amount of a compound having Formula I, II or III.

More specifically, the compounds according to the invention will be useful in the treatment treating diseases of abnormal cell growth and/or dysregulated apoptosis, such as cancer, mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblasitoma, or a combination thereof. Still another embodiment comprises methods of treating mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblasitoma, or a combination of one or more of the above cancers in a patient, said methods comprising administering thereto a therapeutically effective amount of a compound having Formula I, II or III.

The present invention relates also to pharmaceutical compositions comprising at least one compound of Formula I, II or III on its own or in combination with one or more pharmaceutically acceptable excipients.

Among the pharmaceutical compositions according to the invention there may be mentioned more especially those that are suitable for oral, parenteral, nasal, per- or transcutaneous, rectal, perlingual, ocular or respiratory administration, especially tablets or dragees, sublingual tablets, sachets, packets, gelatin capsules, glossettes, lozenges, suppositories, creams, ointments, dermal gels, and drinkable or injectable ampoules.

The dosage varies according to the sex, age and weight of the patient, the route of administration, the nature of the therapeutic indication, or any associated treatments, and ranges from 0.01 mg to 1 g per 24 hours in one or more administrations.

Moreover, the present invention relates also to the combination of a compound of Formula I, II or III with one or more anticancer agents selected from cytotoxic agents, mitotic poisons, anti-metabolites, proteasome inhibitors and kinase inhibitors, and to the use of that type of combination in the manufacture of medicaments for use in the treatment of cancer.

The compounds of the invention may also be used in combination with radiotherapy in the treatment of cancer.

Compounds having Formula I, II or III are also expected to be useful as chemotherapeutic agents in combination with therapeutic agents that include, but are not limited to, angiogenesis inhibitors, antiproliferative agents, kinase inhibitors, receptor tyrosine kinase inhibitors, aurora kinase inhibitors, polo-like kinase inhibitors, bcr-abl kinase inhibitors, growth factor inhibitors, COX-2 inhibitors, non-steroidal anti-inflammatory drugs (NSAIDS), antimitotic agents, alkylating agents, antimetabolites, intercalating antibiotics, platinum containing agents, growth factor inhibitors, ionizing radiation, cell cycle inhibitors, enzymes, topoisomerase inhibitors, biologic response modifiers, immunologicals, antibodies, hormonal therapies, retinoids/deltoids plant alkaloids, proteasome inhibitors, HSP-90 inhibitors, histone deacetylase inhibitors (HDAC) inhibitors, purine analogs, pyrimidine analogs, MEK inhibitors, CDK inhibitors, ErbB2 receptor inhibitors, mTOR inhibitors and combinations thereof as well as other antitumor agents.

Angiogenesis inhibitors include, but are not limited to, EGFR inhibitors, PDGFR inhibitors, VEGFR inhibitors, TTE2 inhibitors, IGF1R inhibitors, matrix metalloproteinase 2 (MMP-2) inhibitors, matrix metalloproteinase 9 (MMP-9) inhibitors, thrombospondin analogs such as thrombospondin-1 and N—Ac-Sar-Gly-Val-D-allolle-Thr-Nva-He-Arg-Pro-NHCH$_2$CH$_3$ or a salt thereof and analogues of N—Ac-Sar-Gly-Val-D-allolle-Thr-Nva-Ile-Arg-PrO-NHCH$_2$CH$_3$ such as N—Ac-GlyVal-D-alle-Ser-Gln-Ile-Arg-ProNHCH$_2$CH$_3$ or a salt thereof.

Examples of EGFR inhibitors include, but are not limited to, Iressa (gefitinib), Tarceva (erlotinib or OSI-774), Icotinib, Erbitux (cetuximab), EMD-7200, ABX-EGF, HR3, IgA antibodies, TP-38 (IVAX), EGFR fusion protein, EGF-vaccine, anti-EGFr immunoliposomes and Tykerb (lapatinib).

Examples of PDGFR inhibitors include, but are not limited to, CP-673,451 and CP-868596.

Examples of VEGFR inhibitors include, but are not limited to, Avastin (bevacizumab), Sutent (sunitinib, SUI 1248), Nexavar (sorafenib, BAY43-9006), CP-547,632, axitinib (AG13736), Apatinib, cabozantinib, Zactima (vandetanib, ZD-6474), AEE788, AZD-2171, VEGF trap, Vatalanib (PTK-787, ZK-222584), Macugen, M862, Pazopanib (GW786034), ABT-869 and angiozyme.

Examples of thrombospondin analogs include, but are not limited to, TSP-I and ABT-510.

Examples of aurora kinase inhibitors include, but are not limited to, VX-680, AZD-1152 and MLN-8054. Example of polo-like kinase inhibitors include, but are not limited to, BI-2536.

Examples of bcr-abl kinase inhibitors include, but are not limited to, Gleevec (imatinib) and Dasatinib (BMS354825).

Examples of platinum containing agents includes, but are not limited to, cisplatin, Paraplatin (carboplatin), eptaplatin, lobaplatin, nedaplatin, Eloxatin (oxaliplatin) or satraplatin.

Examples of mTOR inhibitors includes, but are not limited to, CCI-779, rapamycin, temsirolimus, everolimus, RAD001, INK-128 and ridaforolimus.

Examples of HSP-90 inhibitors includes, but are not limited to, geldanamycin, radicicol, 17-AAG, KOS-953, 17-DMAG, CNF-101, CNF-1010, 17-AAG-nab, NCS-683664, Mycograb, CNF-2024, PU3, PU24FC1, VER49009, IPI-504, SNX-2112 and STA-9090.

Examples of histone deacetylase inhibitors (HDAC) includes, but are not limited to, Suberoylanilide hydroxamic acid (SAHA), MS-275, valproic acid, TSA, LAQ-824, Trapoxin, tubacin, tubastatin, ACY-1215 and Depsipeptide.

Examples of MEK inhibitors include, but are not limited to, PD325901, ARRY-142886, ARRY-438162 and PD98059.

Examples of CDK inhibitors include, but are not limited to, flavopyridol, MCS-5A, CVT-2584, seliciclib (CYC-202, R-roscovitine), ZK-304709, PHA-690509, BMI-1040, GPC-286199, BMS-387,032, PD0332991 and AZD-5438.

Examples of COX-2 inhibitors include, but are not limited to, CELEBREX™ (celecoxib), parecoxib, deracoxib, ABT-963, MK-663 (etoricoxib), COX-189 Lumiracoxib), BMS347070, RS 57067, NS-398, Bextra (valdecoxib), paracoxib, Vioxx (rofecoxib), SD-8381, 4-Methyl-2-(3,4-dimethylphenyl)-1-(4-sulfamoyl-phenyl-1H-pyrrole, T-614, JTE-522, S-2474, SVT-2016, CT-3, SC-58125 and Arcoxia (etoricoxib).

Examples of non-steroidal anti-inflammatory drugs (NSAIDs) include, but are not limited to, Salsalate (Amigesic), Diflunisal (Dolobid), Ibuprofen (Motrin), Ketoprofen (Orudis), Nabumetone (Relafen), Piroxicam (Feldene), Naproxen (Aleve, Naprosyn), Diclofenac (Voltaren), Indomethacin (Indocin), Sulindac (Clinoril), Tolmetin (Tolectin), Etodolac (Lodine), Ketorolac (Toradol) and Oxaprozin (Daypro).

Examples of ErbB2 receptor inhibitors include, but are not limited to, CP-724-714, CI-1033, (canertinib), Herceptin (trastuzumab), Omitarg (2C4, petuzumab), TAK-165, GW-572016 (lonafarnib), GW-282974, EKB-569, PI-166, dHER2 (HER2 Vaccine), APC8024 (HER2 Vaccine), anti-HER/2neu bispecific antibody, B7.her2IgG3, AS HER2 trifunctional bispecfic antibodies, mAB AR-209 and mAB 2B-1.

Examples of alkylating agents include, but are not limited to, nitrogen mustard N-oxide, cyclophosphamide, ifosfamide, trofosfamide, Chlorambucil, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustine, glufosfamide, KW-2170, mafosfamide, and mitolactol, carmustine (BCNU), lomustine (CCNU), Busulfan, Treosulfan, Decarbazine and Temozolomide.

Examples of antimetabolites include but are not limited to, methotrexate, 6-mercaptopurine riboside, mercaptopurine, uracil analogues such as 5-fluorouracil (5-FU) alone or in combination with leucovorin, tegafur, UFT, doxifluridine, carmofur, cytarabine, cytarabine ocfosfate, enocitabine, S-I, Alimta (premetrexed disodium, LY231514, MTA), Gemzar (gemcitabine), fludarabine, 5-azacitidine, capecitabine, cladribine, clofarabine, decitabine, eflornithine, ethnylcytidine, cytosine arabinoside, hydroxyurea, TS-I, melphalan, nelarabine, nolatrexed, ocfosate, disodium premetrexed, pentostatin, pelitrexol, raltitrexed, triapine, trimetrexate, vidarabine, vincristine, vinorelbine, mycophenolic acid, tiazofurin, Ribavirin, EICAR, hydroxyurea and deferoxamine.

Examples of antibiotics include intercalating antibiotics but are not limited to, aclarubicin, actinomycins such as actinomycin D, amrubicin, annamycin, adriamycin, bleomycin a, bleomycin b, daunorubicin, doxorubicin, elsamitrucin, epirbucin, glarbuicin, idarubicin, mitomycin C, nemorubicin, neocarzinostatin, peplomycin, pirarubicin, rebeccamycin, stimalamer, streptozocin, valrubicin, zinostatin and combinations thereof.

Examples of topoisomerase inhibiting agents include, but are not limited to, one or more agents selected from the group consisting of aclarubicin, amonafide, belotecan, camptothecin, 10-hydroxycamptothecin, 9-aminocamptothecin, diflomotecan, irinotecan HCL (Camptosar), edotecarin, epirubicin (Ellence), etoposide, exatecan, gimatecan, lurtotecan, orathecin (Supergen), BN-80915, mitoxantrone, pirarbucin, pixantrone, rubitecan, sobuzoxane, SN-38, tafluposide and topotecan.

Examples of antibodies include, but are not limited to, Rituximab, Cetuximab, Bevacizumab, Trastuzimab, specific CD40 antibodies and specific IGFIR antibodies, Examples of hormonal therapies include, but are not limited to, exemestane (Aromasin), leuprolide acetate, anastrozole (Arimidex), fosrelin (Zoladex), goserelin, doxercalciferol, fadrozole, formestane, tamoxifen citrate (tamoxifen), Casodex, Abarelix, Trelstar, finasteride, fulvestrant, toremifene, raloxifene, lasofoxifene, letrozole, flutamide, bicalutamide, megesterol, mifepristone, nilutamide, dexamethasone, predisone and other glucocorticoids.

Examples of retinoids/deltoids include, but are not limited to, seocalcitol (EB 1089, CB 1093), lexacalcitrol (KH 1060), fenretinide, Aliretinoin, Bexarotene and LGD-1550.

Examples of plant alkaloids include, but are not limited to, vincristine, vinblastine, vindesine and vinorelbine.

Examples of proteasome inhibitors include, but are not limited to, bortezomib (Velcade), MGI 32, NPI-0052 and PR-171.

Examples of immunologicals include, but are not limited to, interferons and numerous other immune enhancing agents. Interferons include interferon alpha, interferon alpha-2a, interferon, alpha-2b, interferon beta, interferon gamma-1a, interferon gamma-1b (Actimmune), or interferon gamma-nl and combinations thereof. Other agents include filgrastim, lentinan, sizofilan, TheraCys, ubenimex, WF-10, aldesleukin, alemtuzumab, BAM-002, decarbazine, daclizumab, denileukin, gemtuzumab ozogamicin, ibritumomab, imiquimod, lenograstim, lentinan, melanoma vaccine (Corixa), molgramostim, OncoVAC-CL, sargaramostim, tasonermin, tecleukin, thymalasin, tositumomab, Virulizin, Z-100, epratuzumab, mitumomab, oregovomab, pemtumomab (Y-muHMFG1), Provenge (Dendreon), CTLA4 (cytotoxic lymphocyte antigen 4) antibodies and agents capable of blocking CTLA4 such as MDX-010.

Examples of biological response modifiers are agents that modify defense mechanisms of living organisms or biological responses, such as survival, growth, or differentiation of tissue cells to direct them to have anti-tumor activity. Such agents include krestin, lentinan, sizofrran, picibanil and ubenimex.

Examples of pyrimidine analogs include, but are not limited to, 5-Fluorouracil, Floxuridine, Doxifluridine, Ratitrexed, cytarabine (ara C), Cytosine arabinoside, Fludarabine, and Gemcitabine.

Examples of purine analogs include but are not limited to, Mercaptopurine and thioguanine.

Examples of antimitotic agents include, but are not limited to, ABT-751, paclitaxel, docetaxel, epothilone D (KOS-862) and ZK-EPO.

Compounds of the present invention are also intended to be used as a radiosensitizer that enhances the efficacy of radiotherapy. Examples of radiotherapy include but are not limited to, external beam radiotherapy (XBRT), or teletherapy, brachtherapy or sealed source radiotherapy, unsealed source radiotherapy.

Compounds of the present invention can also be used in combination with a different class of Bcl-2 inhibitors, such as ABT263 or ABT737.

The present invention will be more readily understood by referring to the following examples which are given to illustrate the invention rather than to limit its scope.

Synthesis

Compounds of the present invention may be made by the following synthetic scheme:

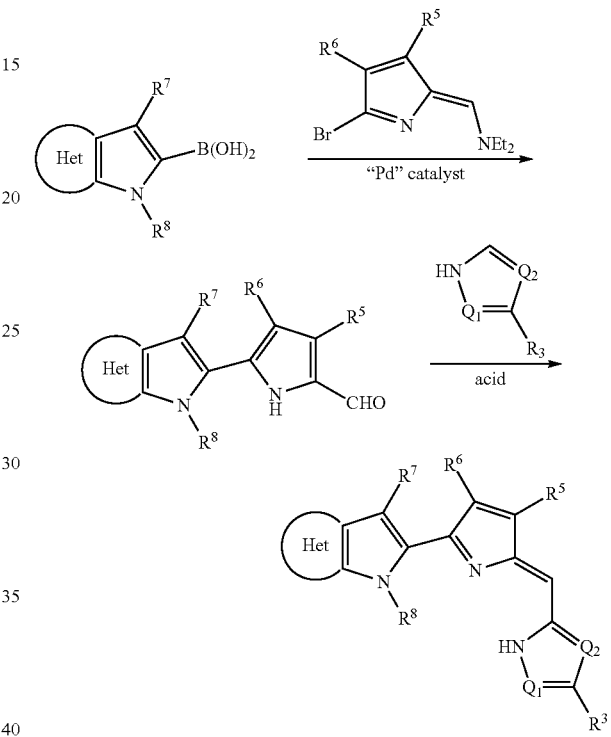

It is meant to be understood that the order of the steps in the processes may be varied, that reagents, solvents and reaction conditions may be substituted for those specifically mentioned, and that vulnerable moieties may be protected and deprotected, as necessary.

The following abbreviations have the meanings indicated. DBU means 1,8-diazabicyclo[5.4.0]undec-7-ene; DIBAL means diisobutylaluminum hydride; DIEA means diisopropylethylamine; DMAP means N,N-dimethylaminopyridine; DME means 1,2-dimethoxyethane; DMF means N,N-dimethylformamide; dmpe means 1,2-bis(dimethylphosphino) ethane; DMSO means dimethylsulfoxide; dppb means 1,4-bis(diphenylphosphino)butane; dppe means 1,2-bis (diphenylphosphino)ethane; dppf means 1,r-bis (diphenylphosphino)ferrocene; dppm means 1,l-bis (diphenylphosphino)methane; EDCI means 1-(3-dimethylaminopropyl)-3-ethylcarbodiimide; HATU means O-(7-azabenzotriazol-l-yl)-N,NTSr'N'-tetramethyluronium hexafluorophosphate; HMPA means hexamethylphosphoramide; IPA means isopropyl alcohol; LDA means lithium diisopropylamide; LHMDS means lithium bis(hexamethyldisilylamide); LAH means lithium aluminum hydride; NCS means N-chlorosuccinimide; PyBOP means benzotriazol-1-yloxytripyrrolidinophosphonium hexafluorophosphate; TDA-I means tris(2-(2-methoxyethoxy)ethyl)amine;

TEA means triethylamine; TFA means trifluoroacetic acid; THF means tetrahydrofuran; NCS means N-chlorosuccinimide; NMM means N-methylmorpholine; NMP means N-methylpyrrolidine; PPh₃ means triphenylphosphine; r.t. means room temperature.

The following preparations and Examples illustrate the invention but do not limit it in any way.

EXAMPLE 1

(Z)-2-(2-((3,5-dimethyl-1H-pyrrol-2-yl)methylene)-3-methoxy-2H-pyrrol-5-yl)-1H-pyrrolo[2,3-b]pyridine

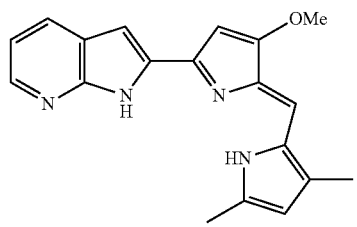 [SMILES: COC1=CC(c2cc3cccnc3[nH]2)=N/C1=C\c1[nH]c(C)cc1C]

Step 1 tert-butyl
1H-pyrrolo[2,3-b]pyridine-1-carboxylate

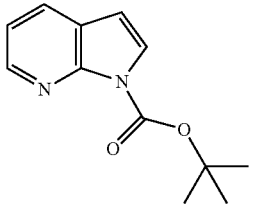 [SMILES: CC(C)(C)OC(=O)n1ccc2cccnc21]

To a solution of 1H-pyrrolo[2,3-b]pyridine (5 g) in 30 mL of THF was added 50 mg of DMAP and 10 g of (Boc)₂O. The reaction mixture was stirred for 1 h at r.t., and 1 g of additional (Boc)₂O was added. After stirring for 1 h at r.t., 1 mL of water was added and the reaction mixture was stirred for another 0.5 h before concentrated. The crude product was co-evaporated with 2×100 mL of toluene to give 10 g of the title compound as oil.

¹H NMR (300 MHz, CDCl₃): δ 8.50 (1H, dd), 7.88 (1H, dd), 7.62 (1H, d), 7.18 (1H, dd), 6.50 (1H, d).

Step 2 1-(tert-butoxycarbonyl)-1H-pyrrolo[2,3-b]pyridin-2-ylboronic acid

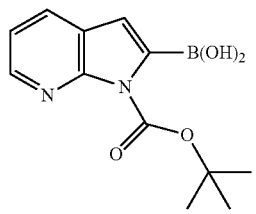 [SMILES: CC(C)(C)OC(=O)n1c(B(O)O)cc2cccnc21]

To a solution of tert-butyl 1H-pyrrolo[2,3-b]pyridine-1-carboxylate (2.18 g, 10 mmol) and B(OiPr)₃ (2.8 mL, 12.1 mmol) in 10 mL of THF cooled at 0° C. was added a LDA solution (16 mmol, prepared from 2.24 mL of iPr₂NH, 15 mL of THF and 6.4 mL of 2.5 M n-BuLi solution in hexane) by a syringe pump over a period of 2 h. The reaction mixture was stirred for additional 1 h at 0° C. before being quenched by addition of 30 mL of pH 7 sodium phosphate buffer solution. The product was extracted with 2×100 mL of EtOAc. The extracts were dried over Na₂SO₄, filtered, and concentrated under vacuum to give 3 g of the title compounds as a gray solid which was used for the next step without further purification.

Step 3 3-methoxy-5-(1H-pyrrolo[2,3-b]pyridin-2-yl)-1H-pyrrole-2-carbaldehyde

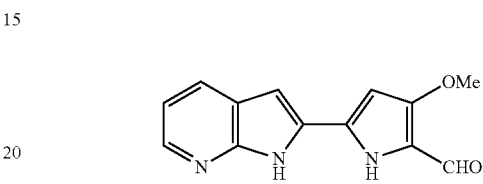

A mixture of 1-(tert-butoxycarbonyl)-1H-pyrrolo[2,3-b]pyridin-2-ylboronic acid (150 mg, 0.57 mmol), N-((5-bromo-3-methoxy-2H-pyrrol-2-ylidene)methyl)-N-ethylethanamine (114 mg, 0.44 mmol, provided by Chemzon Scientific Inc, Montreal, Canada), Pd(dppf)₂Cl₂CH₂Cl₂ (16 mg, 0.02 mmol) and K₃PO₄ (187 mg, 0.88 mmol) in a 20 mL sealed-tube flask was vented 4 times with nitrogen. 1,4-Dioxane (2.2 mL) and water (0.3 mL) were introduced by syringe and the mixture was vented twice with nitrogen. The reaction mixture was then heated at 80° C. for 2 h and TLC showed no starting materials were left. EtOH (15 mL) and water (5 mL) were added and the reaction mixture was stirred for 0.5 h at r.t. and then extracted with 2×15 mL of EtOAc. The extracts were dried over Na₂SO₄, filtered through a pad of silica gel. The filtrate was concentrated under vacuum to give 15 mg of the title compound as a dark solid.

¹H NMR (300 MHz, DMSO-d₆): δ 11.92 (2H, bs), 9.48 (1H, s), 8.22 (1H, d), 7.95 (1H, d), 7.12 (1H, s), 7.08 (1H, dd), 6.70 (1H, s), 3.88 (3H, s).

Step 4 (Z)-2-(2-((3,5-dimethyl-1H-pyrrol-2-yl)methylene)-3-methoxy-2H-pyrrol-5-yl)-1H-pyrrolo[2,3-b]pyridine

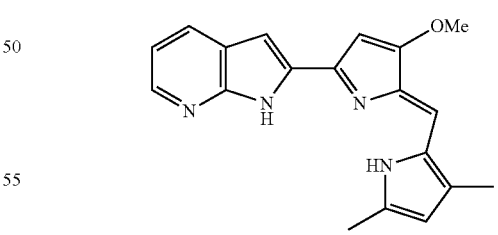

To a solution of 3-methoxy-5-(1H-pyrrolo[2,3-b]pyridin-2-yl)-1H-pyrrole-2-carbaldehyde (8 mg) and 2,4-dimethyl-1H-pyrrole (3.2 mg) in 1 mL of MeOH was added 2 small drops of a solution of 2 N HCl in ether. The dark-red reaction solution was stirred at r.t. for 1 h and then quenched with 3 mL of pH 7 sodium phosphate buffer solution. The product was extracted with 2×5 mL of EtOAc. The combined extracts were dried over Na₂SO₄, filtered, and concentrated. The residue was purified by Combiflash on a silica gel column eluted with a gradient up to 80% EtOAc/hexanes to give 8 mg of the title compound as a dark solid.

$^1$H NMR (300 MHz, CDCl$_3$): δ 8.31 (1H, dd), 7.89 (1H, dd), 7.00 (1H, s), 7.00 (1H, t), 6.85 (1H, s), 6.13 (1H, s), 5.82 (1H, s), 3.95 (3H, s), 2.23 (3H, s), 2.07 (3H, s).

MS (CI, positive): m/e 319.3 (M+1)$^+$.

EXAMPLE 2

(Z)-2-chloro-5-(2-((3,5-dimethyl-1H-pyrrol-2-yl)methylene)-3-methoxy-2H-pyrrol-5-yl)-4H-thieno[3,2-b]pyrrole

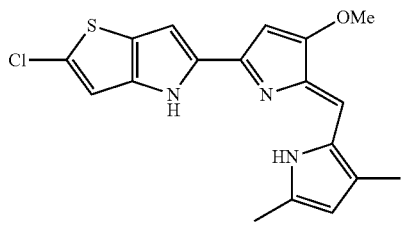 [SMILES: COC1=CC(c2cc3sc(Cl)cc3[nH]2)=N/C1=C\c1[nH]c(C)cc1C]

Step 1 2-chloro-4H-thieno[3,2-b]pyrrole

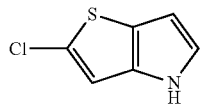

A solution of 2-chloro-4H-thieno[3,2-b]pyrrole-5-carboxylic acid (4 g, prepared by following the procedure described in WO2002/20530), and 0.7 g of Cu powder in 45 mL of quinoline was vented once with nitrogen, and then heated at 160° C. under nitrogen atmosphere for 2 h. The reaction mixture was cooled to r.t. and treated with 150 mL of 3N HCl and diluted with 100 mL of 1:1 EtOAc/hexane. The reaction mixture was then filtered through a pad of silica gel and the filter cake was washed with 200 mL of 1:1 EtOAc/hexanes. The organic phase was separated and washed with 200 mL of brine and dried over Na$_2$SO$_4$. After filtration and concentration, 3.5 g of the crude title compound was obtained as brown oil which was used for the next step without further purification.

$^1$H NMR (300 MHz, acetone-d$_6$): δ 7.10 (1H, d), 7.03 (1H, s), 6.35 (1H, d).

Step 2 tert-butyl 2-chloro-4H-thieno[3,2-b]pyrrole-4-carboxylate

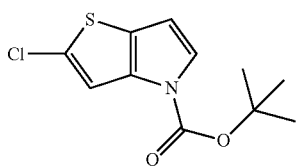 [SMILES: CC(C)(C)OC(=O)n1ccc2sc(Cl)cc21]

To a solution of 2-chloro-4H-thieno[3,2-b]pyrrole (3 g) in 25 mL of THF was added 3.6 g of (Boc)$_2$O. After stirring at r.t. for 0.5 h, additional 1 g of (Boc)$_2$O was added and the reaction mixture was stirred for another hour, and then treated with 1 mL of water. The reaction mixture was then concentrated and the residue was purified by Combiflash on a silica gel column eluted with a gradient of up to 5% EtOAc/hexanes to give 4.5 g of the title compound as a solid.

$^1$H NMR (300 MHz, CDCl$_3$): δ 7.38 (1H, 2d), 7.23 (1H, 2d), 6.43 and 6.41 (1H, 2 s), 1.65 (9H, s).

Step 3 4-(tert-butoxycarbonyl)-2-chloro-4H-thieno[3,2-b]pyrrol-5-ylboronic acid

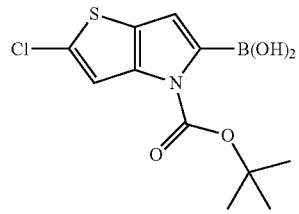 [SMILES: CC(C)(C)OC(=O)n1c(B(O)O)cc2sc(Cl)cc21]

To a solution of tert-butyl 2-chloro-4H-thieno[3,2-b]pyrrole-4-carboxylate (0.52 g, 2 mmol) and B(OiPr)$_3$ (0.7 mL, 3 mmol) in 10 mL of THF cooled at 0° C. was added a LDA solution (4 mmol, prepared from 0.56 mL of iPr$_2$NH, 5.84 mL of THF and 1.6 mL of 2.5 M n-BuLi solution in hexane) by a syringe pump over a period of 2 h. The reaction mixture was stirred for additional 6 h at 0° C. before being quenched by addition of 20 mL of saturated NH$_4$Cl solution. The product was extracted with 2×20 mL of EtOAc, dried over Na$_2$SO$_4$, filtered and concentrated. The residue was purified by Combiflash on a silica gel column eluted with a gradient of up to 60% EtOAc/hexanes to give 0.3 g of the title compound as a solid.

$^1$H NMR (300 MHz, CDCl$_3$): δ 7.29 (1H, s), 7.15 (1H, s), 6.97 (2H, s), 1.71 (9H, s).

Step 4 tert-butyl 2-chloro-5-(5-formyl-4-methoxy-1H-pyrrol-2-yl)-4H-thieno[3,2-b]pyrrole-4-carboxylate

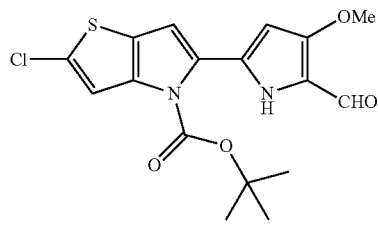 [SMILES: COc1cc(-c2cc3sc(Cl)cc3n2C(=O)OC(C)(C)C)[nH]c1C=O]

A mixture of 4-(tert-butoxycarbonyl)-2-chloro-4H-thieno[3,2-b]pyrrol-5-ylboronic acid (200 mg, 0.66 mmol), N-((5-bromo-3-methoxy-2H-pyrrol-2-ylidene)methyl)-N-ethylethanamine (160 mg, 0.61 mmol, provided by Chemzon Scientific Inc, Montreal, Canada), Pd(dppf)$_2$Cl$_2$CH$_2$Cl$_2$ (18 mg) and K$_3$PO$_4$ (260 mg) in a 20 mL sealed-tube flask was vented 4 times with nitrogen. 1,4-Dioxane (3 mL and water (0.4 mL) were introduced by syringes and the mixture was vented twice with nitrogen. The reaction mixture was heated at 80° C. for 1 h and TLC showed no starting materials were left. After being cooled to r.t., the reaction mixture was treated with 3 mL of 1N HCl, and stirred for 3 h. The mixture was then extracted with 20 mL of EtOAc, and the extract was dried over $Na_2SO_4$, filtered through a pad of silica gel. The filtrate was concentrated under vacuum and the residue was purified by Combiflash on a silica gel column eluted with a gradient of up to 60% EtOAc/hexanes to give 11 mg of the title compound as a solid.

$^1$H NMR (300 MHz, $CDCl_3$): δ 9.55 (1H, s), 7.20 (1H, s), 6.82 (1H, s), 6.11 (1H, s), 3.90 (3H, s), 1.66 (9H, s).

Step 5 (Z)-tert-butyl 2-chloro-5-(2-((3,5-dimethyl-1H-pyrrol-2-yl)methylene)-3-methoxy-2H-pyrrol-5-yl)-4H-thieno[3,2-b]pyrrole-4-carboxylate

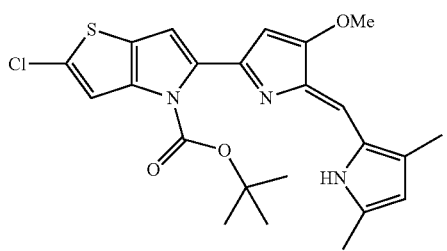 [SMILES: COC1=CC(c2cc3sc(Cl)cc3n2C(=O)OC(C)(C)C)=N/C1=C\c1[nH]c(C)cc1C]

To a solution of tert-butyl 2-chloro-5-(5-formyl-4-methoxy-1H-pyrrol-2-yl)-4H-thieno[3,2-b]pyrrole-4-carboxylate (11 mg) and 2,4-dimethyl-1H-pyrrole (3.5 mg) in 1 mL of MeOH was added 2 small drops of a solution of 2 N HCl in ether. The dark-red reaction solution was stirred at r.t. for 10 min and then quenched with 3 mL of pH 7 sodium phosphate buffer solution. The product was extracted with 2×5 mL of EtOAc. The combined extracts were dried over $Na_2SO_4$, filtered, and concentrated. The residue was purified by Combiflash on a silica gel column eluted with a gradient up to 60% EtOAc/hexanes to give 10 mg of the title compound as a dark solid.

Step 6 (Z)-2-chloro-5-(2-((3,5-dimethyl-1H-pyrrol-2-yl)methylene)-3-methoxy-2H-pyrrol-5-yl)-4H-thieno[3,2-b]pyrrole

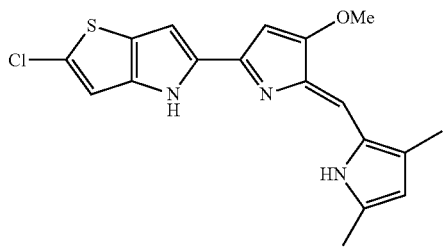 [SMILES: COC1=CC(c2cc3sc(Cl)cc3[nH]2)=N/C1=C\c1[nH]c(C)cc1C]

A solution of (Z)-tert-butyl 2-chloro-5-(2-((3,5-dimethyl-1H-pyrrol-2-yl)methylene)-3-methoxy-2H-pyrrol-5-yl)-4H-thieno[3,2-b]pyrrole-4-carboxylate (10 mg) in 2 mL of 88% aqueous formic acid solution was sonicated in an ultrasonic bath for 1 h and then concentrated in vacuo. The residue was purified by Combiflash on a silica gel column eluted with a gradient up to 70% EtOAc/hexanes to give 5 mg of the title compound as a dark solid.

$^1$H NMR (300 MHz, acetone-$d_6$): δ 7.70 (1H, s), 6.97 (1H, s), 6.85 (1H, s), 6.27 (1H, s), 5.86 (1H, s), 3.94 (3H, s), 2.27 (3H, s), 2.20 (3H, s).

MS (CI, positive): m/e 358.1 (M+1)$^+$.

EXAMPLE 3

Biochemical Evaluation

Anti-oncogenic effects of the compounds of the present invention were evaluated by cell viability (proliferation) assays in H460 non-small cell lung cancer cell line and A549 human lung carcinoma cell line. H460 and A549 were purchased from ATCC (American Type Culture Collection), and they were maintained in RPMI 1640 and DMEM, respectively, with 10% fetal bovine serum. Cell lines were cultured in an incubator with 5% $CO_2$ at 37° C.

Cells were seeded in 6-well-plates ($10^5$ cells/ml medium per well) and allowed them to grow for 24 hrs in the incubator. Cells were then treated with 1 µM of tested compounds. Cells treated with 1% DMSO were used as control. 72 hours after treatment, cells were removed by trypsinization and viable cell number was obtained by counting Trypan blue-excluding cells under microscope with a hemocytometer. Experiments were performed in triplicate. Statistical were carried out by analysis of variance (ANOVA) and LSD test for multiple comparisons, with p<0.05 considered significant.

| Compound | Cell Death (%) after 3-day treatment Cell Line | |
|---|---|---|
| @ 1 µM | H460 | A549 |
| EXAMPLE 2 | 88.6% | 86.7% |
| Obatoclax | 88.3% | 76.6% |

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A compound of Formula II

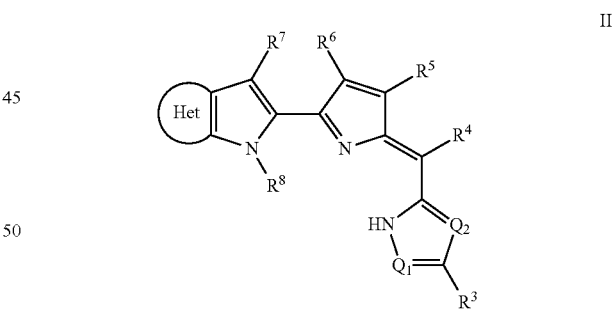

or a pharmaceutically acceptable salt thereof, wherein:
$Q_1$ is —C($R^1$)— or —N—;
$Q_2$ is —C($R^2$)— or —N—;
$R^1$, $R^2$, and $R^3$ are independently —$Y_m(R_b)$, wherein $R_b$ is —H, halogen, —$NH_2$, —CN, —$NO_2$, —SH, —$N_3$, —$C_1$-$C_8$ alkyl, —O—($C_1$-$C_8$ alkyl), —$C_2$-$C_8$ alkenyl, —$C_2$-$C_8$ alkynyl, —$C_3$-$C_{12}$ cycloalkyl, -aryl, -heteroaryl, -3- to 9-membered heterocycle, —$OR^9$, —O($CH_2$)$_n$$OR^9$, —C(O)$R^9$, —O—C(O)$R^9$, —C(O)($CH_2$)$_n$—$R^9$, —O—C(O)$OR^9$, —O—C(O)NH$R^9$, —O—C(O)N($R^9$)$_2$, —C(O)N($R^9$)$_2$, —C(O)$OR^9$, —C(O)NH$R^9$, —S—$R^9$, —S(O)$R^9$, —S(O)$_2R^9$, —NHC(O)$R^9$, —NHS(O)$_2R^9$, —O—C(S)$R^9$, —O—C (S)OR⁹, —O—C(S)NHR⁹, O—C(S)N(R⁹)₂, —C(S)OR⁹, —C(S)NHR⁹, —C(S)N(R⁹)₂, —NHC(S)R⁹, —NR⁹C(S)R⁹, —NHC(S)NHR⁹, —NHC(S)N(R⁹)₂, —NR⁹C(S)NHR⁹, —NR⁹C(S)N(R⁹)₂ or R¹ and R³, or R² and R³, together with the carbon atom to which each is attached, may join to form a 5- to 9-membered ring which is unsubstituted or substituted by 1 to 3 hetero atoms;

R⁴ is —H, halogen, —OH, —NH₂, —C₁-C₈ alkyl, or —O—(C₁-C₈ alkyl);

R⁵ is —Y_m—(R_n), wherein —R_c is —C₁-C₈ alkyl, —O—(C₁-C₈ alkyl), —O-benzyl, —OH, —NH₂, —NH(C₁-C₅ alkyl), —N(C₁-C₅ alkyl)₂, —NH(aryl), —N(aryl)₂, —NH(heteroaryl), —N(heteroaryl)₂, —CN, —NO₂, —N₃, —C₂-C₈ alkynyl, —OR⁹, —O(CH₂)ₙOR⁹, —C(O)R₉, —O—C(O)R⁹, —C(O)(CH₂)_a—R⁹, —O—C(O)OR⁹, —O—C(O)NHR⁹, —O—C(O)N(R⁹)₂, —C(O)N(R⁹)₂, —C(O)OR⁹, —C(O)NHR⁹, —S—R⁹, —S(O)R⁹, —S(O)₂R⁹, —NHC(O)R⁹, —NHS(O)₂R⁹, —O—C(S)R⁹, —O—C(S)OR⁹, —O—C(S)NHR⁹, O—C(S)N(R⁹)², —C(S)OR⁹, —C(S)NHR⁹, —C(S)N(R⁹)2, —NHC(S)R⁹, —NR⁹C(S)R⁹, —NHC(S)NHR⁹, —NHC(S)N(R⁹)₂, —NR⁹C(S)NHR⁹, —NR⁹C(S)N(R⁹)₂;

R⁶ is —Y_m(R_d), wherein —R_d is —H, —OH, halogen, amino, -aryl, -heteroaryl, —NH(C₁-C₅ alkyl), —N(C₁-C₅ alkyl)₂, —NH(aryl), —N(aryl)₂, —NH(heteroaryl), —N(heteroaryl)₂, —CN, —NO₂, —N₃, —C₁-C₈ alkyl, —O—(C₁-C₈ alkyl), —(C₁-C₈ alkyl)-OH, —C₂-C₈ alkenyl, —C₂-C₈ alkynyl, —C₃-C₁₂ cycloalkyl, -aryl, -heteroaryl, -3- to 9-membered heterocycle, —OR⁹, —O(CH₂)ₙOR⁹, —C(O)R⁹, —O—C(O)R⁹, —C(O)(CH₂)—R⁹, —O—C(O)OR⁹, —O—C(O)NHR⁹, —O—C(O)N(R⁹)2, —C(O)N(R⁹)₂, —C(O)OR⁹, —C(O)NHR⁹, —S—R⁹, —S(O)R⁹, —S(O)₂R⁹, —NHC(O)R⁹, —NHS(O)₂R⁹, —O—C(S)R⁹, —O—C(S)OR⁹, —O—C(S)NHR⁹, O—C(S)N(R⁹)₂, —C(S)OR⁹, —C(S)NHR⁹, —C(S)N(R⁹)₂, —NHC(S)R⁹, —NR⁹C(S)R⁹, —NHC(S)NHR⁹, —NHC(S)N(R⁹)₂, —NR⁹C(S)NHR⁹, —NR⁹C(S)N(R⁹)₂;

R⁷ is —Y_m(R_e), wherein —R_e is —H, halogen, —NH₂, C₁-C₈ alkyl, -aryl, -heteroaryl, —NH(C₁-C₅ alkyl), —N(C₁-C₅ alkyl)₂, —NH(aryl), —N(aryl)₂, —NH(heteroaryl), —N(heteroaryl)₂, —C(O)NH(C₁-C₅ alkyl), —C(O)N(C₁-C₅ alkyl)₂, —NHC(O)(C₁-C₅ alkyl), —NHC(=NH2⁺)NH₂, —CN, —NO₂, —N₃, -3- to 9-membered heterocycle, —OR⁹, —O(CH₂)ₙOR⁹, —C(O)R⁹, —O—C(O)R⁹, —C(O)(CH₂)_a—R⁹, —O—C(O)OR⁹, —O—C(O)NHR⁹, —O—C(O)N(R⁹)₂, —C(O)N(R⁹)₂, —C(O)OR⁹, —C(O)NHR⁹, —S—R⁹, —S(O)R⁹, —S(O)₂R⁹, —NHC(O)R⁹, —NHS(O)₂R⁹, —O—C(S)R₉, —O—C(S)OR⁹, —O—C(S)NHR⁹, O—C(S)N(R⁹)₂, —C(S)OR⁹, —C(S)NHR⁹, —C(S)N(R⁹)₂, —NHC(S)R⁹, —NR⁹C(S)R⁹, —NHC(S)NHR⁹, —NHC(S)N(R⁹)₂, —NR⁹C(S)NHR⁹, —NR⁹C(S)N(R⁹)₂;

R⁸ is —Y_m(R_a), wherein —R_a is —H, —OH, —C₁-C₈ alkyl, —C₂-C₈ alkenyl, —C₂-C₈ alkynyl, —C₃-C₁₂ cycloalkyl, -aryl, -heteroaryl, -3- to 9-membered heterocycle, —OR⁹, —O(CH₂)OR⁹, —C(O)R⁹, —O—C(O)R⁹, —C(O)(CH₂)—R⁹, —O—C(O)OR⁹, —O—C(O)NHR⁹, —O—C(O)N(R⁹)², —C(O)N(R⁹)₂, —C(O)OR⁹, —C(O)NHR⁹, —S—R⁹, —S(O)R⁹, —S(O)₂R⁹, —NHC(O)R⁹, —NHS(O)₂R⁹, —O—C(S)R⁹, —O—C(S)OR⁹, —O—C(S)NHR⁹, O—C(S)N(R⁹)₂, —C(S)OR⁹, —C(S)NHR⁹, —C(S)N(R⁹)₂, —NHC(S)R⁹, —NR⁹C(S)R⁹, —NHC(S)NHR⁹, —NHC(S)N(R⁹)₂, —NR⁹C(S)NHR⁹, —NR⁹C(S)N(R⁹)₂;

R⁹ is independently —H, —C₁-C₈ alkyl, —C₃-C₁₂ cycloalkyl, -aryl, -heteroaryl, -3- to 9-membered heterocycle, —C₂-C₈ alkenyl, or —C₂-C₈ alkynyl;

wherein

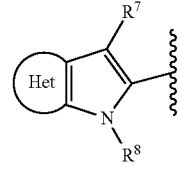

is selected from the from the following 5,5-bicyclic moieties:

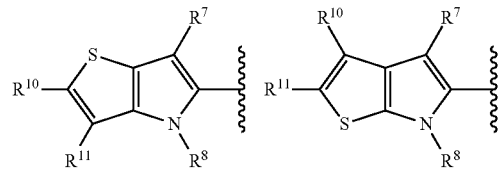

wherein

R¹⁰, and R¹¹ are independently —Y_m(R_f), wherein —R_f is —H, halogen, —NH₂, C₁-C₈ alkyl, —NH(C₁-C₅ alkyl), —N(C₁-C₅ alkyl)₂, -aryl, -heteroaryl, —NH(aryl), —N(aryl)₂, —NH(heteroaryl), —N(heteroaryl)₂, —C(O)NH(C₁-C₅ alkyl), —C(O)N(C₁-C₅ alkyl)₂, —NHC(O)(C₁-C₅ alkyl), —NHC(=NH₂⁺)NH₂, —CN, —NO₂, N₃, -3- to 9-membered heterocycle, —OR⁹, —O(CH₂)ₙOR⁹, —C(OH)R⁹₂, —CH(OH)R⁹, —C(O)R⁹, —O—C(O)R⁹, —C(O)(CH₂)—R⁹, —O—C(O)OR⁹, —O—C(O)NHR⁹, —O—C(O)N(R⁹)₂, —C(O)N(R⁹)₂, —C(O)OR⁹, —C(O)NHR⁹, —S—R⁹, —S(O)R⁹, —S(O)₂R⁹, —NHC(O)R⁹, —NHS(O)₂R⁹, —O—C(S)R⁹, —O—C(S)OR⁹, —O—C(S)NHR⁹, O—C(S)N(R⁹)₂, —C(S)OR⁹, —C(S)NHR⁹, —C(S)N(R⁹)₂, —NHC(S)R⁹, —NR⁹C(S)R⁹, —NHC(S)NHR⁹, —NHC(S)N(R⁹)₂, —NR⁹C(S)NHR⁹, —NR⁹C(S)N(R⁹)₂;

wherein when R¹⁰ and R¹¹ together with the carbon atom to which each is attached, may join to form a 5- to 9-membered carbocycle or heterocycle;

each Y is independently —C₁-C₈ alkylene-, —C₂-C₈ alkenylene- or —C₂-C₈ alkynylene-;

each m is independently 0 or 1; and each n is independently an integer ranging from 0 to 6.

2. A compound of Formula IIa

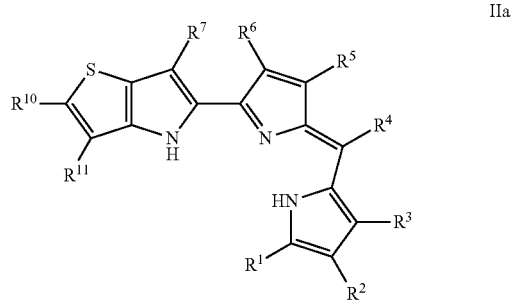

or a pharmaceutically acceptable salt thereof, wherein:

R¹, R², and R³ are independently —Y_m(R_b), wherein R_b is —H, halogen, —NH₂, —CN, —NO₂, —SH, —N₃, —C₁-C₈ alkyl, —O—(C₁-C₈ alkyl), —C₂-C₈ alkenyl, —$C_2$-$C_8$ alkynyl, —$C_3$-$C_{12}$ cycloalkyl, -aryl, -heteroaryl, -3- to 9-membered heterocycle, —$OR^9$, —$O(CH_2)_nOR^9$, —$C(O)R^9$, —O—$C(O)R^9$, —$C(O)(CH_2)_n$—$R^9$, —O—$C(O)OR^9$, —O—$C(O)NHR^9$, —O—$C(O)N(R^9)_2$, —$C(O)N(R^9)_2$, —$C(O)OR^9$, —$C(O)NHR^9$, —S—$R^9$, —$S(O)R^9$, —$S(O)_2R^9$, —$NHC(O)R^9$, —$NHS(O)_2R^9$, —O—$C(S)R^9$, —O—C(S)$OR^9$, —O—C(S)$NHR^9$, O—$C(S)N(R^9)_2$, —$C(S)OR^9$, —$C(S)NHR^9$, —$C(S)N(R^9)_2$, —$NHC(S)R^9$, —$NR^9C(S)R^9$, —$NHC(S)NHR^9$, —$NHC(S)N(R^9)_2$, —$NR^9C(S)NHR^9$, —$NR^9C(S)N(R^9)_2$ or $R^1$ and $R^3$, or $R^2$ and $R^3$, together with the carbon atom to which each is attached, may join to form a 5- to 9-membered ring which is unsubstituted or substituted by 1 to 3 hetero atoms, $R^4$ is —H, halogen, —OH, —$NH_2$, —$C_1$-$C_8$ alkyl, or —O—($C_1$-$C_8$ alkyl);

$R^5$ is —$Y_m(R_c)$, wherein —$R_c$ is —$C_1$-$C_8$ alkyl, —O—($C_1$-$C_8$ alkyl), —O-benzyl, —OH, —$NH_2$, —$NH(C_1$-$C_5$ alkyl), —$N(C_1$-$C_5$ alkyl)$_2$, —NH(aryl), —N(aryl)$_2$, —NH(heteroaryl), —N(heteroaryl)$_2$, —CN, —$NO_2$, —$N_3$, —$C_2$-$C_8$ alkynyl, —$OR^9$, —$O(CH_2)_nOR^9$, —$C(O)R_9$, —O—$C(O)R^9$, —$C(O)(CH_2)_n$—$R^9$, —O—$C(O)OR^9$, —O—$C(O)NHR^9$, —O—$C(O)N(R^9)_2$, —$C(O)N(R^9)_2$, —$C(O)OR^9$, —$C(O)NHR^9$, —S—$R^9$, —$S(O)R^9$, —$S(O)_2R^9$, —$NHC(O)R^9$, —$NHS(O)_2R^9$, —O—$C(S)R^9$, —O—C(S)$OR^9$, —O—C(S)$NHR^9$, O—$C(S)N(R^9)^2$, —$C(S)OR^9$, —$C(S)NHR^9$, —$C(S)N(R^9)2$, —$NHC(S)R^9$, —$NR^9C(S)R^9$, —$NHC(S)NHR^9$, —$NHC(S)N(R^9)_2$, —$NR^9C(S)NHR^9$, —$NR^9C(S)N(R^9)_2$;

$R^6$ is —$Y_m(R_d)$, wherein —$R_d$ is —H, —OH, halogen, amino, -aryl, -heteroaryl, —$NH(C_1$-$C_5$ alkyl), —$N(C_1$-$C_5$ alkyl)$_2$, —NH(aryl), —N(aryl)$_2$, —NH(heteroaryl), —N(heteroaryl)$_2$, —CN, —$NO_2$, —$N_3$, —$C_1$-$C_8$ alkyl, —O—($C_1$-$C_8$ alkyl), —($C_1$-$C_8$ alkyl)-OH, —$C_2$-$C_8$ alkenyl, —$C_2$-$C_8$ alkynyl, —$C_3$-$C_{12}$ cycloalkyl, -aryl, heteroaryl, -3- to 9-membered heterocycle, —$OR^9$, —$O(CH_2)_nOR^9$, —$C(O)R^9$, —O—$C(O)R^9$, —$C(O)(CH_2)_n$—$R^9$, —O—$C(O)OR^9$, —O—$C(O)NHR^9$, —O—$C(O)N(R^9)2$, —$C(O)N(R^9)_2$, —$C(O)OR^9$, —$C(O)NHR^9$, —S—$R^9$, —$S(O)R^9$, —$S(O)_2R^9$, —$NHC(O)R^9$, —$NHS(O)_2R^9$, —O—$C(S)R^9$, —O—C(S)$OR^9$, —O—C(S)$NHR^9$, O—$C(S)N(R^9)_2$, —$C(S)OR^9$, —$C(S)NHR^9$, —$C(S)N(R^9)_2$, —$NHC(S)R^9$, —$NR^9C(S)R^9$, —$NHC(S)NHR^9$, —$NHC(S)N(R^9)_2$, —$NR^9C(S)NHR^9$, —$NR^9C(S)N(R^9)_2$;

$R^7$ is —$Y_m(R_e)$, wherein —$R_e$ is —H, halogen, —$NH_2$, $C_1$-$C_8$ alkyl, -aryl, -heteroaryl, —$NH(C_1$-$C_5$ alkyl), —$N(C_1$-$C_5$ alkyl)$_2$, —NH(aryl), —N(aryl)$_2$, —NH(heteroaryl), —N(heteroaryl)$_2$, —$C(O)NH(C_1$-$C_5$ alkyl), —$C(O)N(C_1$-$C_5$ alkyl)$_2$, —$NHC(O)(C_1$-$C_5$ alkyl), —NHC(=$NH2^+$)$NH_2$, —CN, —$NO_2$, $N_3$, -3- to 9-membered heterocycle, —$OR^9$, —$O(CH_2)_nOR^9$, —$C(O)R^9$, —O—$C(O)R^9$, —$C(O)(CH_2)_n$—$R^9$, —O—$C(O)OR^9$, —O—$C(O)NHR^9$, —O—$C(O)N(R^9)_2$, —$C(O)N(R^9)_2$, —$C(O)OR^9$, —$C(O)NHR^9$, —S—$R^9$, —$S(O)R^9$, —$S(O)_2R^9$, —$NHC(O)R^9$, —$NHS(O)_2R^9$, —O—$C(S)R_9$, —O—C(S)$OR^9$, —O—C(S)$NHR^9$, O—$C(S)N(R^9)_2$, —$C(S)OR^9$, —$C(S)NHR^9$, —$C(S)N(R^9)_2$, —$NHC(S)R^9$, —$NR^9C(S)R^9$, —$NHC(S)NHR^9$, —$NHC(S)N(R^9)_2$, —$NR^9C(S)NHR^9$, —$NR^9C(S)N(R^9)_2$;

$R^9$ is independently —H, —$C_1$-$C_8$ alkyl, —$C_1$-$C_8$ halogenated-alkyl, —$C_3$-$C_{12}$ cycloalkyl, -aryl, -heteroaryl, -3- to 9-membered heterocycle, —$C_2$-$C_8$ alkenyl, or —$C_2$-$C_8$ alkynyl;

$R^{10}$, and $R^{11}$ are independently —$Y_m(R_f)$, wherein —$R_f$ is —H, halogen, —$NH_2$, $C_1$-$C_8$ alkyl, —$NH(C_1$-$C_5$ alkyl), —$N(C_1$-$C_5$ alkyl)$_2$, -aryl, -heteroaryl, —NH(aryl), —N(aryl)$_2$, —NH(heteroaryl), —N(heteroaryl)$_2$, —$C(O)NH(C_1$-$C_5$ alkyl), —$C(O)N(C_1$-$C_5$ alkyl)$_2$, —$NHC(O)(C_1$-$C_5$ alkyl), —NHC(=$NH_2^+$)$NH_2$, —CN, —$NO_2$, $N_3$, -3- to 9-membered heterocycle, —$OR^9$, —$O(CH_2)_nOR^9$, —$C(OH)R^9_2$, —$CH(OH)R^9$, —$C(O)R^9$, —O—$C(O)R^9$, —$C(O)(CH_2)_n$—$R^9$, —O—$C(O)OR^9$, —O—$C(O)NHR^9$, —O—$C(O)N(R^9)_2$, —$C(O)N(R^9)_2$, —$C(O)OR^9$, —$C(O)NHR^9$, —S—$R^9$, —$S(O)R^9$, —$S(O)_2R^9$, —$NHC(O)R^9$, —$NHS(O)_2R^9$, —O—$C(S)R^9$, —O—C(S)$OR^9$, —O—C(S)$NHR^9$, O—$C(S)N(R^9)_2$, —$C(S)OR^9$, —$C(S)NHR^9$, —$C(S)N(R^9)_2$, —$NHC(S)R^9$, —$NR^9C(S)R^9$, —$NHC(S)NHR^9$, —$NHC(S)N(R^9)_2$, —$NR^9C(S)NHR^9$, —$NR^9C(S)N(R^9)_2$;

$R^{10}$ and $R^{11}$, together with the carbon atom to which each is attached, can form a 5- to 9-membered carbocycle or heterocycle;

each Y is independently —$C_1$-$C_8$ alkylene-, —$C_2$-$C_8$ alkenylene- or —$C_2$-$C_8$ alkynylene-;

each m is independently 0 or 1; and each n is independently an integer ranging from 0 to 6.

3. A compound of Formula IIb

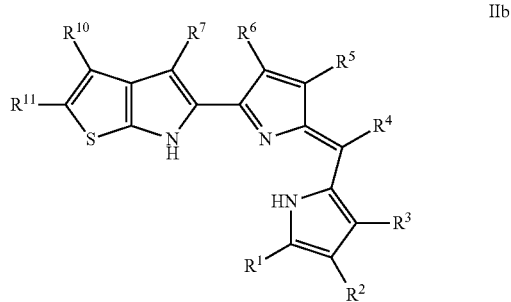

IIb or a pharmaceutically acceptable salt thereof, wherein:

$R^1$, $R^2$, and $R^3$ are independently —$Y_m(R_b)$, wherein $R_b$ is —H, halogen, —$NH_2$, —CN, —$NO_2$, —SH, —$N_3$, —$C_1$-$C_8$ alkyl, —O—($C_1$-$C_8$ alkyl), —$C_2$-$C_8$ alkenyl, —$C_2$-$C_8$ alkynyl, —$C_3$-$C_{12}$ cycloalkyl, -aryl, -heteroaryl, -3- to 9-membered heterocycle, —$OR^9$, —$O(CH_2)_nOR^9$, —$C(O)R^9$, —O—$C(O)R^9$, —$C(O)(CH_2)_n$—$R^9$, —O—$C(O)OR^9$, —O—$C(O)NHR^9$, —O—$C(O)N(R^9)_2$, —$C(O)N(R^9)_2$, —$C(O)OR^9$, —$C(O)NHR^9$, —S—$R^9$, —$S(O)R^9$, —$S(O)_2R^9$, —$NHC(O)R^9$, —$NHS(O)_2R^9$, —O—$C(S)R^9$, —O—C(S)$OR^9$, —O—C(S)$NHR^9$, O—$C(S)N(R^9)_2$, —$C(S)OR^9$, —$C(S)NHR^9$, —$C(S)N(R^9)_2$, —$NHC(S)R^9$, —$NR^9C(S)R^9$, —$NHC(S)NHR^9$, —$NHC(S)N(R^9)_2$, —$NR^9C(S)NHR^9$, —$NR^9C(S)N(R^9)_2$ or $R^1$ and $R^3$, or $R^2$ and $R^3$, together with the carbon atom to which each is attached, join to form a 5- to 9-membered ring which is unsubstituted or substituted by 1 to 3 hetero atoms, $R^4$ is —H, halogen, —OH, —$NH_2$, —$C_1$-$C_8$ alkyl, or —O—($C_1$-$C_8$ alkyl);

$R^5$ is —$Y_m$—($R_c$), wherein —$R_c$ is —$C_1$-$C_8$ alkyl, —O—($C_1$-$C_8$ alkyl), —O-benzyl, —OH, —$NH_2$, —$NH(C_1$-$C_5$ alkyl), —$N(C_1$-$C_5$ alkyl)$_2$, —NH(aryl), —N(aryl)$_2$, —NH(heteroaryl), —N(heteroaryl)$_2$, —CN, —$NO_2$, —$N_3$, —$C_2$-$C_8$ alkynyl, —$OR^9$, —$O(CH_2)_nOR^9$, —$C(O)R_9$, —O—$C(O)R^9$, —$C(O)(CH_2)_n$—$R^9$, —O—$C(O)OR^9$, —O—$C(O)NHR^9$, —O—$C(O)N (R⁹)₂, —C(O)N(R⁹)₂, —C(O)OR⁹, —C(O)NHR⁹, —S—R⁹, —S(O)R⁹, —S(O)₂R⁹, —NHC(O)R⁹, —NHS(O)₂R⁹, —O—C(S)R⁹, —O—C(S)OR⁹, —O—C(S)NHR⁹, O—C(S)N(R⁹)₂, —C(S)OR⁹, —C(S)NHR⁹, —C(S)N(R⁹)₂, —NHC(S)R⁹, —NR⁹C(S)R⁹, —NHC(S)NHR⁹, —NHC(S)N(R⁹)₂, —NR⁹C(S)NHR⁹, —NR⁹C(S)N(R⁹)₂;

R⁶ is —Y$_m$(R$_d$), wherein —R$_d$ is —H, —OH, halogen, amino, -aryl, -heteroaryl, —NH(C₁-C₅ alkyl), —N(C₁-C₅ alkyl)₂, —NH(aryl), —N(aryl)₂, —NH(heteroaryl), —N(heteroaryl)₂, —CN, —NO₂, —N₃, —C₁-C₈ alkyl, —O—(C₁-C₈ alkyl), —(C₁-C₈ alkyl)-OH, —C₂-C₈ alkenyl, —C₂-C₈ alkynyl, —C₃-C₁₂ cycloalkyl, -aryl, -heteroaryl, -3- to 9-membered heterocycle, —OR⁹, —O(CH₂)$_n$OR⁹, —C(O)R⁹, —O—C(O)R⁹, —C(O)(CH₂)$_n$—R⁹, —O—C(O)OR⁹, —O—C(O)NHR⁹, —O—C(O)N(R⁹)2, —C(O)N(R⁹)₂, —C(O)OR⁹, —C(O)NHR⁹, —S—R⁹, —S(O)R⁹, —S(O)₂R⁹, —NHC(O)R⁹, —NHS(O)₂R⁹, —O—C(S)R⁹, —O—C(S)OR⁹, —O—C(S)NHR⁹, O—C(S)N(R⁹)₂, —C(S)OR⁹, —C(S)NHR⁹, —C(S)N(R⁹)₂, —NHC(S)R⁹, —NR⁹C(S)R⁹, —NHC(S)NHR⁹, —NHC(S)N(R⁹)₂, —NR⁹C(S)NHR⁹, —NR⁹C(S)N(R⁹)₂;

R⁷ is —Y$_m$(R$_e$), wherein —R$_e$ is —H, halogen, —NH₂, C₁-C₈ alkyl, -aryl, -heteroaryl, —NH(C₁-C₅ alkyl), —N(C₁-C₅ alkyl)₂, —NH(aryl), —N(aryl)₂, —NH(heteroaryl), —N(heteroaryl)₂, —C(O)NH(C₁-C₅ alkyl), —C(O)N(C₁-C₅ alkyl)₂, —NHC(O)(C₁-C₅ alkyl), —NHC(=NH2⁺)NH₂, —CN, —NO₂, N₃, -3- to 9-membered heterocycle, —OR⁹, —O(CH₂)$_n$OR⁹, —C(O)R⁹, —O—C(O)R⁹, —C(O)(CH₂)$_n$—R⁹, —O—C(O)OR⁹, —O—C(O)NHR⁹, —O—C(O)N(R⁹)₂, —C(O)N(R⁹)₂, —C(O)OR⁹, —C(O)NHR⁹, —S—R⁹, —S(O)R⁹, —S(O)₂R⁹, —NHC(O)R⁹, —NHS(O)₂R⁹, —O—C(S)R₉, —O—C(S)OR⁹, —O—C(S)NHR⁹, O—C(S)N(R⁹)₂, —C(S)OR⁹, —C(S)NHR⁹, —C(S)N(R⁹)₂, —NHC(S)R⁹, —NR⁹C(S)R⁹, —NHC(S)NHR⁹, —NHC(S)N(R⁹)₂, —NR⁹C(S)NHR⁹, —NR⁹C(S)N(R⁹)₂;

R⁹ is independently —H, —C₁-C₈ alkyl, —C₃-C₁₂ cycloalkyl, —C₁-C₈ halogenated-alkyl, -aryl, -heteroaryl, -3- to 9-membered heterocycle, —C₂-C₈ alkenyl, or —C₂-C₈ alkynyl;

R¹⁰, and R¹¹ are independently —Y$_m$(R$_f$), wherein —R$_f$ is —H, halogen, —NH₂, C₁-C₈ alkyl, —NH(C₁-C₅ alkyl), —N(C₁-C₅ alkyl)₂, -aryl, -heteroaryl, —NH(aryl), —N(aryl)₂, —NH(heteroaryl), —N(heteroaryl)₂, —C(O)NH(C₁-C₅ alkyl), —C(O)N(C₁-C₅ alkyl)₂, —NHC(O)(C₁-C₅ alkyl), —NHC(=NH₂⁺)NH₂, —CN, —NO₂, N₃, -3- to 9-membered heterocycle, —OR⁹, —O(CH₂)OR⁹, —C(OH)R⁹₂, —CH(OH)R⁹, —C(O)R⁹, —O—C(O)R⁹, —C(O)(CH₂)—R⁹, —O—C(O)OR⁹, —O—C(O)NHR⁹, —O—C(O)N(R⁹)₂, —C(O)N(R⁹)₂, —C(O)OR⁹, —C(O)NHR⁹, —S—R⁹, —S(O)R⁹, —S(O)₂R⁹, —NHC(O)R⁹, —NHS(O)₂R⁹, —O—C(S)R⁹, —O—C(S)OR⁹, —O—C(S)NHR⁹, O—C(S)N(R⁹)₂, —C(S)OR⁹, —C(S)NHR⁹, —C(S)N(R⁹)₂, —NHC(S)R⁹, —NR⁹C(S)R⁹, —NHC(S)NHR⁹, —NHC(S)N(R⁹)₂, —NR⁹C(S)NHR⁹, —NR⁹C(S)N(R⁹)₂;

R¹⁰ and R¹¹, together with the carbon atom to which each is attached, can form a 5- to 9-membered carbocycle or heterocycle;

each Y is independently —C₁-C₈ alkylene-, —C₂-C₈ alkenylene- or —C₂-C₈ alkynylene-;

each m is independently 0 or 1; and each n is independently an integer ranging from 0 to 6.

4. The compound according to any one of claims 1,2 or 3 which is selected from:

(Z)-5-(2-((3,5-dimethyl-1H-pyrrol-2-yl)methylene)-3-methoxy-2H-pyrrol-5-yl)-4H-thieno[3,2-b]pyrrole (Z)-2-chloro-5-(2-((3,5-dimethyl-1H-pyrrol-2-yl)methylene)-3-methoxy-2H-pyrrol-5-yl)-4H-thieno[3,2-b]pyrrole;

(Z)-5-(2-((3,5-dimethyl-1H-pyrrol-2-yl)methylene)-3-methoxy-2H-pyrrol-5-yl)-2-methyl-4H-thieno[3,2-b]pyrrole (Z)-2-bromo-5-(2-((3,5-dimethyl-1H-pyrrol-2-yl)methylene)-3-methoxy-2H-pyrrol-5-yl)-4H-thieno[3,2-b]pyrrole;

(Z)-5-(2-((3,5-dimethyl-1H-pyrrol-2-yl)methylene)-3-methoxy-2H-pyrrol-5-yl)-6H-thieno[2,3-b]pyrrole;

(Z)-5-(2-((3,5-dimethyl-1H-pyrrol-2-yl)methylene)-3-methoxy-2H-pyrrol-5-yl)-2-methyl-6H-thieno[2,3-b]pyrrole;

(Z)-2-chloro-5-(2-((3,5-dimethyl-1H-pyrrol-2-yl)methylene)-3-methoxy-2H-pyrrol-5-yl)-6H-thieno[2,3-b]pyrrole;

(Z)-2-bromo-5-(2-((3,5-dimethyl-1H-pyrrol-2-yl)methylene)-3-methoxy-2H-pyrrol-5-yl)-6H-thieno[2,3-b]pyrrole;

(Z)-2-(5-(2-((3,5-dimethyl-1H-pyrrol-2-yl)methylene)-3-methoxy-2H-pyrrol-5-yl)-4H-thieno[3,2-b]pyrrol-2-yl)propan-2-ol;

(Z)-1-(5-(2-((3,5-dimethyl-1H-pyrrol-2-yl)methylene)-3-methoxy-2H-pyrrol-5-yl)-4H-thieno[3,2-b]pyrrol-2-yl)ethanol;

(Z)-1-(5-(2-((3,5-dimethyl-1H-pyrrol-2-yl)methylene)-3-methoxy-2H-pyrrol-5-yl)-4H-thieno[3,2-b]pyrrol-2-yl)ethanone;

(Z)-1-(5-(2-((3,5-dimethyl-1H-pyrrol-2-yl)methylene)-3-methoxy-2H-pyrrol-5-yl)-4H-thieno[3,2-b]pyrrol-2-yl)propan-1-one;

(Z)-1-(5-(2-((3,5-dimethyl-1H-pyrrol-2-yl)methylene)-3-methoxy-2H-pyrrol-5-yl)-4H-thieno[3,2-b]pyrrol-2-yl)-2-methylpropan-1-one;

(Z)-2-(5-(2-((3,5-dimethyl-1H-pyrrol-2-yl)methylene)-3-methoxy-2H-pyrrol-5-yl)-4H-thieno[3,2-b]pyrrol-2-yl)-1,1,1,3,3,3-hexafluoropropan-2-ol; and (Z)-1-(5-(2-((3,5-dimethyl-1H-pyrrol-2-yl)methylene)-3-methoxy-2H-pyrrol-5-yl)-4H-thieno[3,2-b]pyrrol-2-yl)-2,2,2-trifluoroethanol.

5. A prodrug according to claim 1, having Formula IIIa or IIIb:

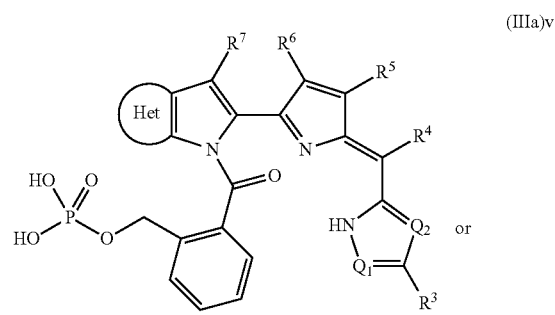

(IIIa)v

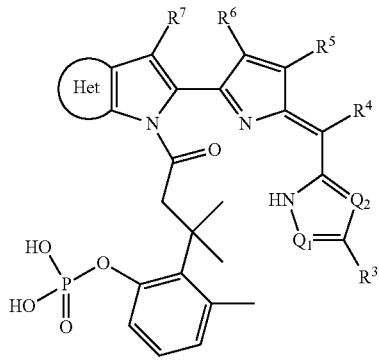

(IIIb)

or a pharmaceutically acceptable salt thereof wherein the

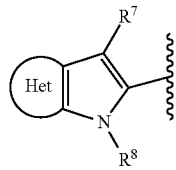

portion and $Q_1$, $Q_2$, $R^3$, $R^4$, $R^5$, $R^6$ and $R^7$ are defined as in claim 1.

6. A composition comprising at least one compound of any one of claims 1,2 or 3 in combination with a pharmaceutically acceptable carrier.

7. A composition comprising at least one compound of any one of claims 1,2 or 3 in combination with an anti-cancer agent selected from the group consisting of a cytotoxic agent, an antimitotic agent, an anti-metabolite, a proteasome inhibitor, an HDAC inhibitor and a kinase inhibitor.

8. A composition comprising at least one compound of claim 4 in combination with a pharmaceutically acceptable carrier.

9. A composition of claim 8, further comprising an anti-cancer agent chosen from a cytotoxic agent, an antimitotic agent, an anti-metabolite, a proteasome inhibitor, an HDAC inhibitor and a kinase inhibitor.

10. A composition comprising at least one prodrug of claim 5 in combination with a pharmaceutically acceptable carrier.

11. A composition of claim 10, further comprising an anti-cancer agent chosen from a cytotoxic agent, an antimitotic agent, an anti-metabolite, a proteasome inhibitor, an HDAC inhibitor and a kinase inhibitor.

\* \* \* \* \*